US008764763B2

(12) United States Patent
Wong et al.

(10) Patent No.: US 8,764,763 B2
(45) Date of Patent: Jul. 1, 2014

(54) PROCEDURE FOR REPAIRING FOOT INJURY

(71) Applicant: Wright Medical Technology, Inc., Arlington, TN (US)

(72) Inventors: Kian-Ming (Kevin) Wong, Cordova, TN (US); Vernon R. Hartdegen, Collierville, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 0 days.

(21) Appl. No.: 13/655,795

(22) Filed: Oct. 19, 2012

(65) Prior Publication Data

US 2013/0103037 A1    Apr. 25, 2013

Related U.S. Application Data

(62) Division of application No. 12/474,991, filed on May 29, 2009, now Pat. No. 8,313,492.

(60) Provisional application No. 61/057,556, filed on May 30, 2008.

(51) Int. Cl.
*A61B 17/58* (2006.01)
*A61B 17/60* (2006.01)
*A61F 2/00* (2006.01)

(52) U.S. Cl.
USPC ............. 606/96; 606/80; 606/87; 606/99; 606/104; 606/105

(58) Field of Classification Search
USPC .......... 606/80, 86 R, 87–88, 96–99, 104, 105
See application file for complete search history.

(56) References Cited

U.S. PATENT DOCUMENTS

| 3,664,022 | A | | 5/1972 | Small |
| 4,235,428 | A | * | 11/1980 | Davis .............................. 606/96 |
| 4,920,958 | A | | 5/1990 | Walt et al. |
| 4,945,904 | A | | 8/1990 | Bolton et al. |
| 5,354,300 | A | | 10/1994 | Goble et al. |
| 5,458,602 | A | | 10/1995 | Goble et al. |
| 5,613,971 | A | | 3/1997 | Lower et al. |
| 5,688,283 | A | | 11/1997 | Knapp |
| 5,743,916 | A | | 4/1998 | Greenberg et al. |
| 5,968,050 | A | | 10/1999 | Torrie |
| 6,019,767 | A | | 2/2000 | Howell |
| 6,287,307 | B1 | | 9/2001 | Abboudi |
| 6,342,056 | B1 | | 1/2002 | Mac-Thiong et al. |

(Continued)

OTHER PUBLICATIONS

Written Opinion of the International Searching Authority bearing a mailing date of Sep. 15, 2009.

*Primary Examiner* — Andrew Yang
*Assistant Examiner* — Olivia C Chang
(74) *Attorney, Agent, or Firm* — Duane Morris LLP

(57) ABSTRACT

A Lisfranc injury between a second metatarsal and medial cuneiform is repaired by gaining access to the injury site and placing two arm members of a novel drill guide around the two neighboring bones at the injury site, drilling a guide wire through the two bones guided by the drill guide to a desired depth, measuring the depth of the guide wire to determine the proper length for a bone screw for securing the two bones, drilling a cannulated drill bit into the two bones to a drill depth using the guide wire as a guide, and threading a bone screw into the two bones.

10 Claims, 20 Drawing Sheets

(56) References Cited

U.S. PATENT DOCUMENTS

| | | |
|---|---|---|
| 6,716,218 B2 | 4/2004 | Holmes et al. |
| 2005/0096656 A1 | 5/2005 | Behrens |
| 2005/0203508 A1* | 9/2005 | Thelen et al. .................. 606/53 |
| 2006/0206044 A1 | 9/2006 | Simon |
| 2006/0241592 A1 | 10/2006 | Myerson et al. |
| 2007/0276400 A1 | 11/2007 | Moore et al. |
| 2008/0058829 A1 | 3/2008 | Buscher et al. |
| 2008/0177302 A1* | 7/2008 | Shurnas ....................... 606/228 |
| 2009/0036893 A1* | 2/2009 | Kartalian et al. ............... 606/60 |

* cited by examiner

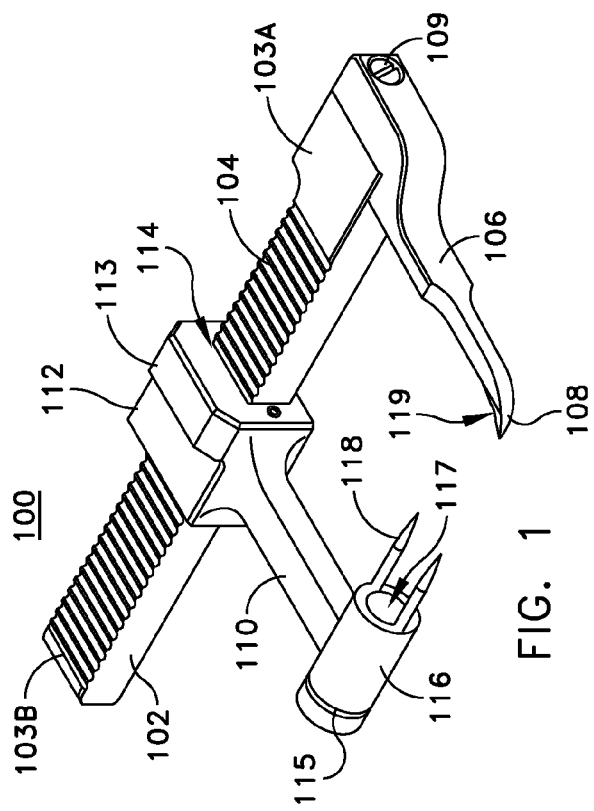
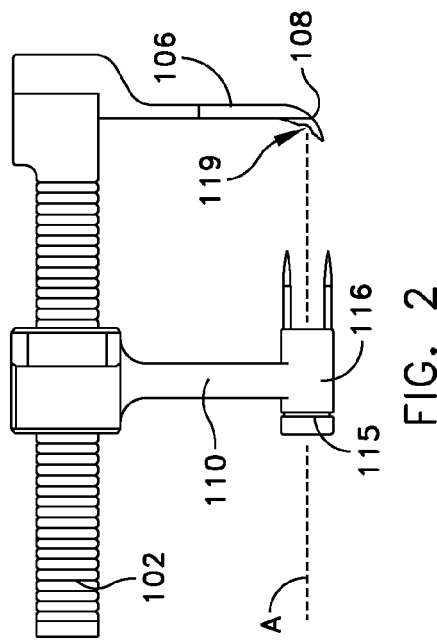
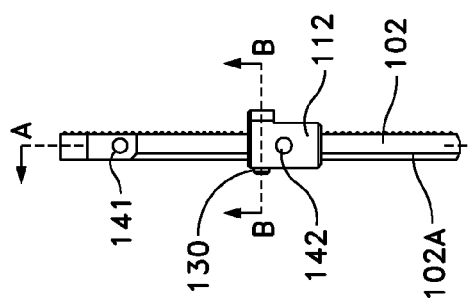
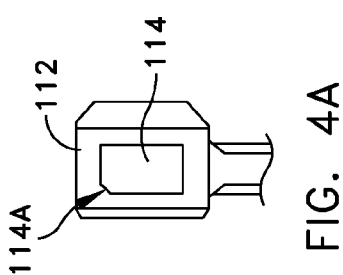
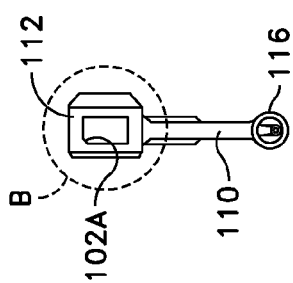
FIG. 1
FIG. 2
FIG. 3
FIG. 4
FIG. 4A

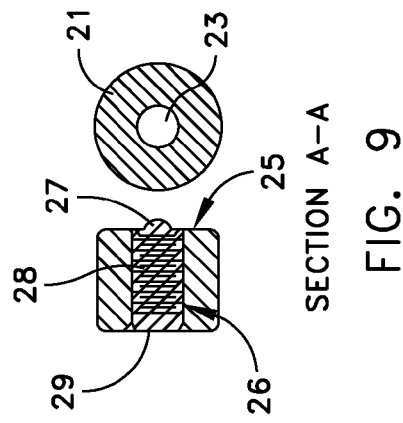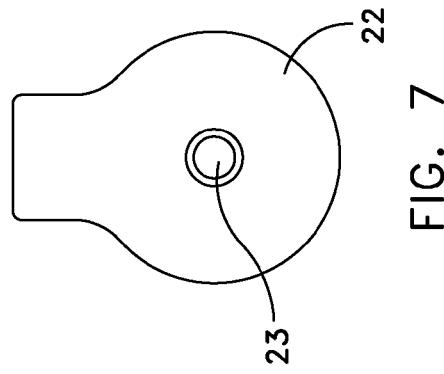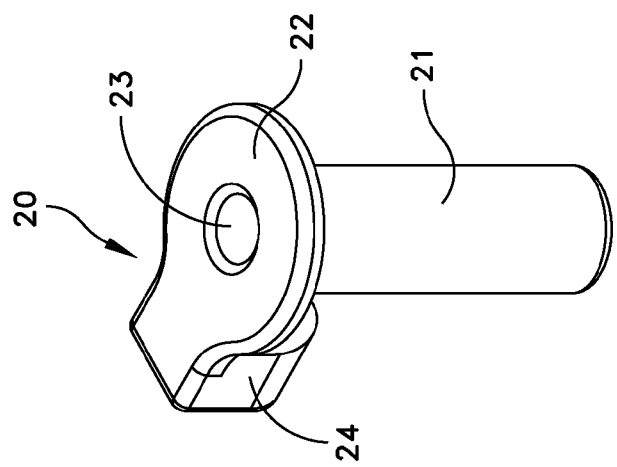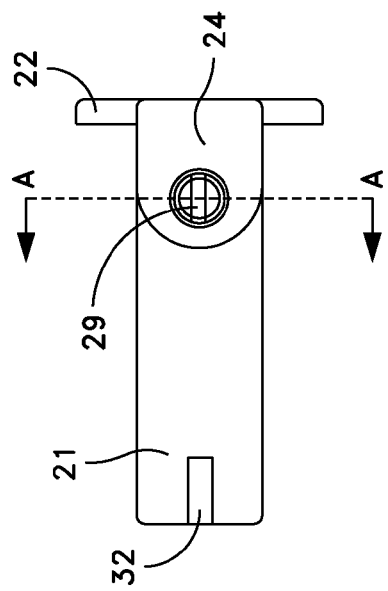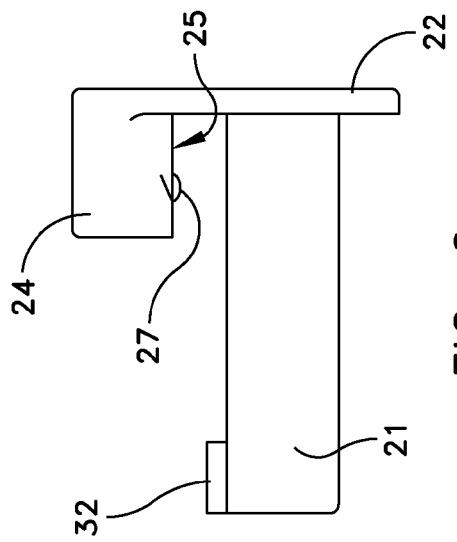

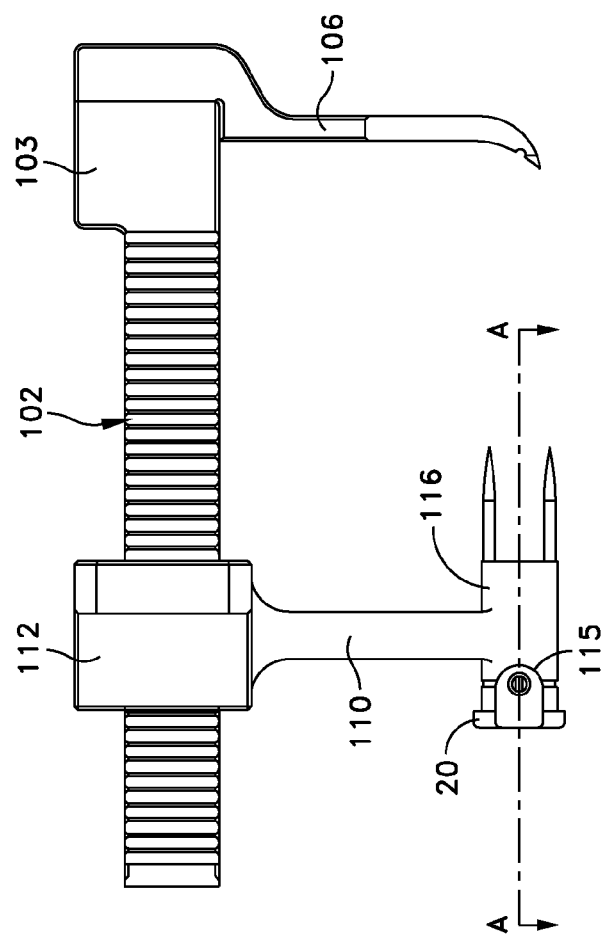
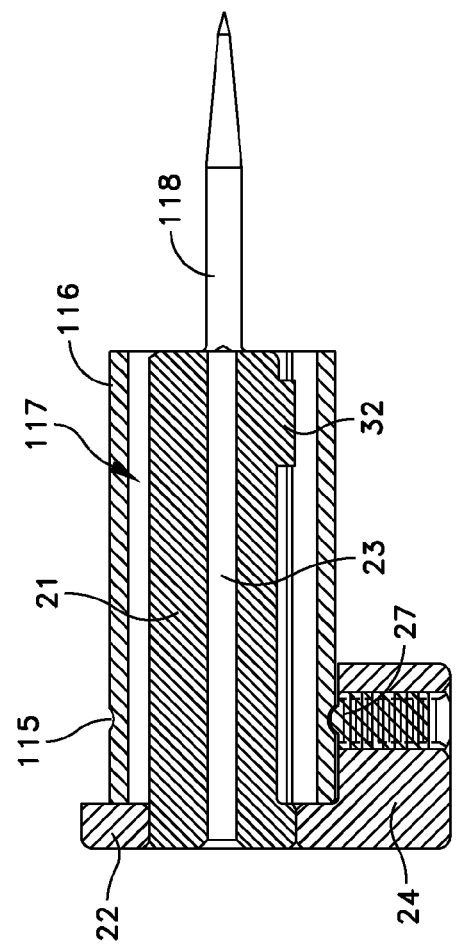
FIG. 10
FIG. 11

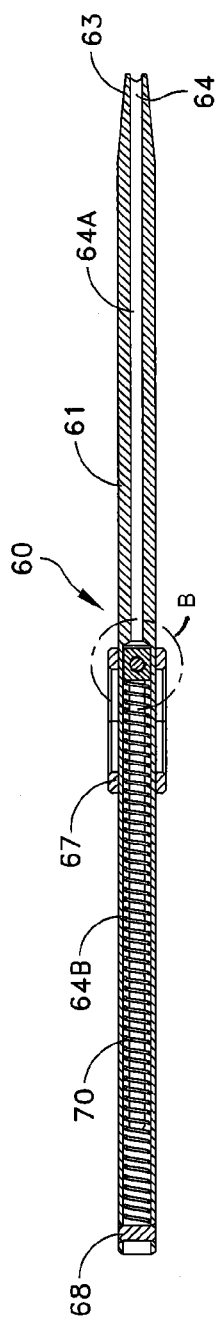
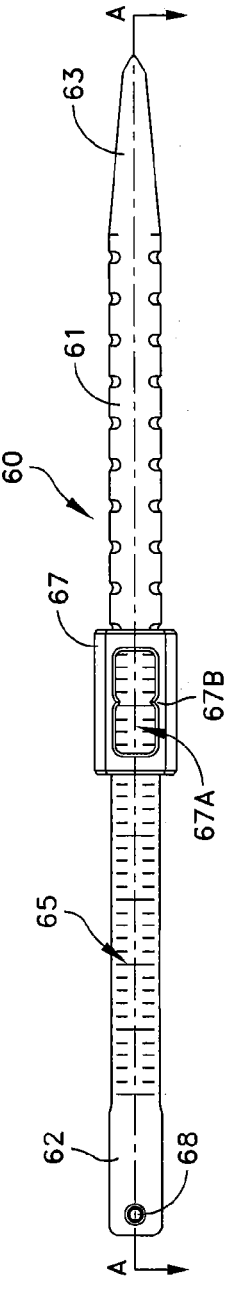
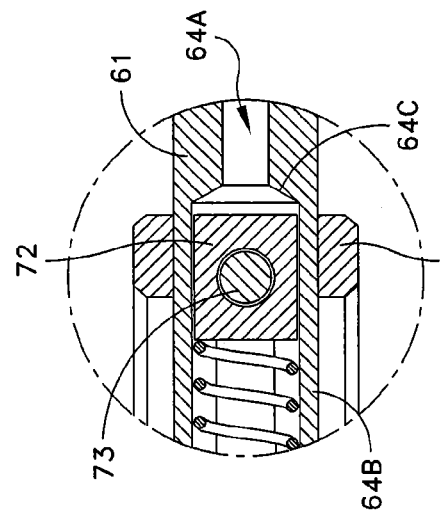
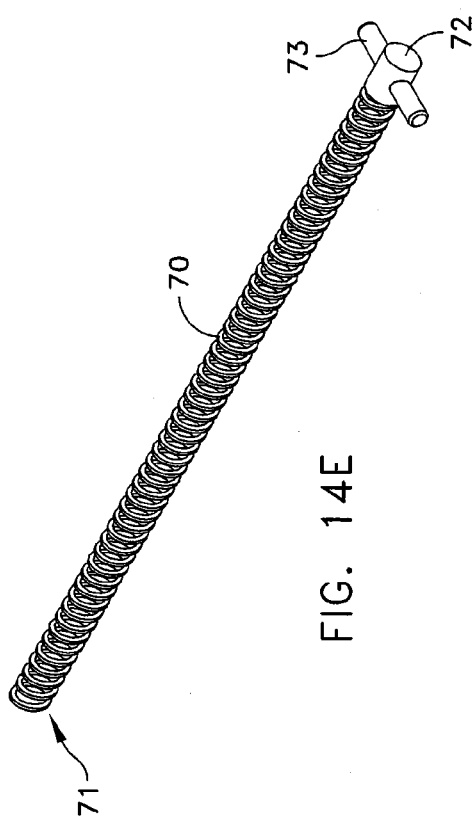
FIG. 14C
FIG. 14B
FIG. 14D
FIG. 14E

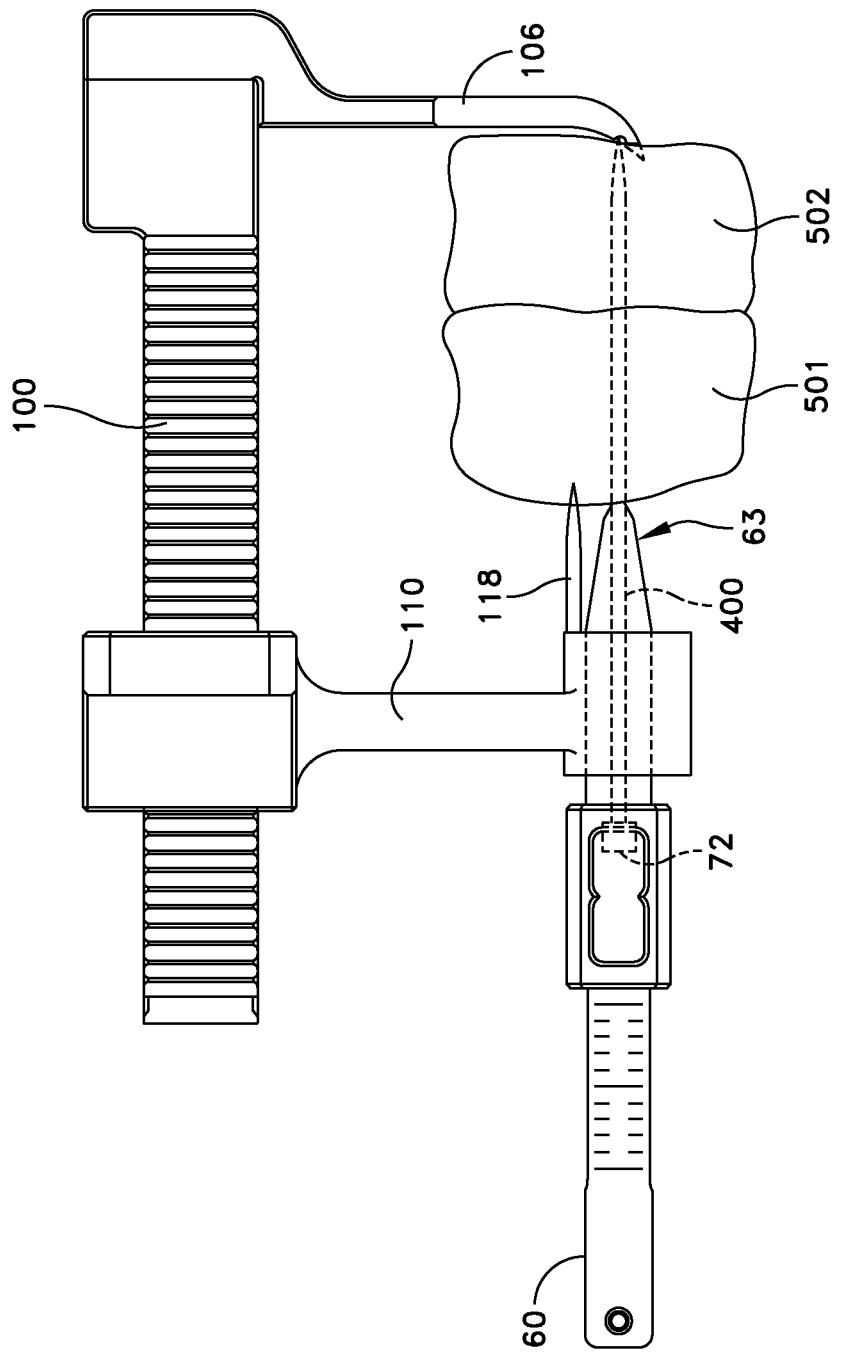

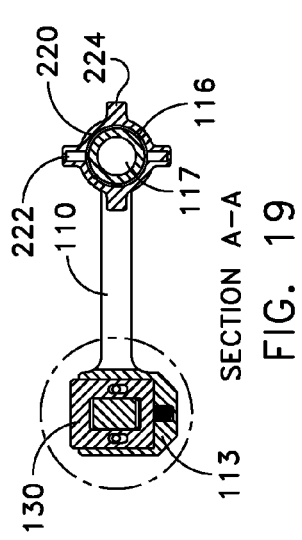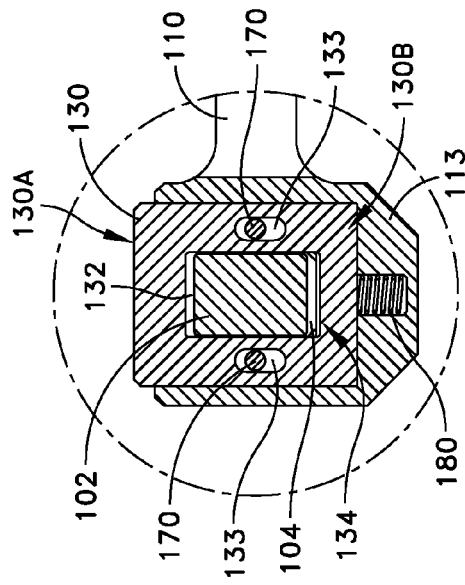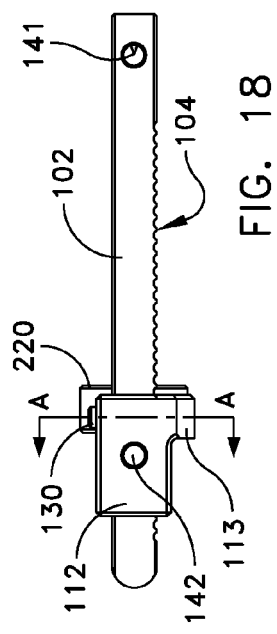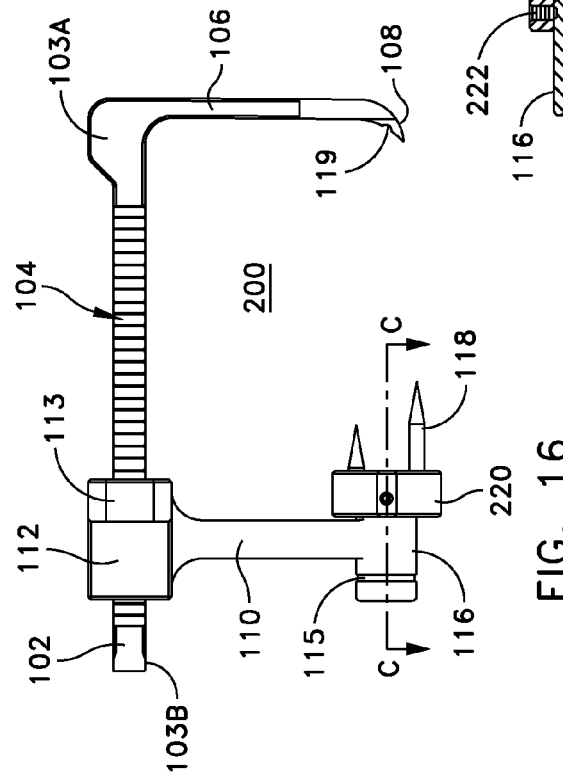

PROCEDURE FOR REPAIRING FOOT INJURY

CROSS-REFERENCE TO RELATED APPLICATION

This application is a divisional application of U.S. application Ser. No. 12/474,991 filed May 29, 2009, now U.S. Pat. No. 8,313,492 issued on Nov. 20, 2012, which claims the benefit under 35 U.S.C. §119(e) of U.S. Provisional Application Ser. No. 61/057,556 filed May 30, 2008, the disclosure of which is incorporated herein by reference in its entirety.

FIELD OF THE INVENTION

The present disclosure relates to a method for repairing damaged or fractured bones in the foot.

BACKGROUND

There has not been any drill alignment guide instrument for use in foot and ankle soft tissues and bone repair applications. Thus, there is a continuing need for a drill alignment guide instrument for use in foot and ankle soft tissues and bone repair applications.

The mid-foot region or the medial column of the foot is comprised of many osseous components—distal phalanx, proximal phalanx, first metatarsal, medial cuneiform, intermediate cuneiform, lateral cuneiform, cuboid, navicular and talus. Bone fractures in the mid-foot regions are generally difficult to fixate because of the geometries of the bones involved. Thus, there is a need for a guiding instrument that can provide guidance for targeting, aligning, measuring and drilling of a hole for placement of a bone screw and then actual placement of the bone screw while holding or compressing the bones in reduction.

SUMMARY

The orthopedic drill guide of the present disclosure provides accurate means for guiding the drilling through foot bones such as cuneiforms or metatarsals to install bone screws for repairing soft tissues and bone fractures. The drill guide of the present disclosure is also configured and adapted to provide compression of the bone pieces while alignment, guiding, measuring, drilling, and screw installation are performed. The drill guide can also be used for syndesmosis applications in the mid-foot and distal tibia.

The drill guide assembly of the present disclosure comprises an elongated body having first and second ends, a first arm member extending from the first end of the elongated body and a second arm member extending from the elongated body and configured and adapted to be longitudinally movable along the elongated body. The second arm member can be moved along the elongated body in two directions, towards or away from the first arm member. The second arm member is provided with a guide housing at its outer end (the end away from the elongated body), the guide housing being configured and adapted to removably receive a sleeve that has a longitudinal bore for receiving a guide wire (such as Kirschner wire, also known as K-wire) or a drill bit.

Present disclosure also includes a depth gage device for measuring the depth of a K-wire that has been drilled into a bone. The depth gage device comprises a cannulated elongated body having first and second ends and a bore longitudinally extending through the length of the elongated body. The bore is closed at the first end of the elongated body and open at the second end of the elongated body. The open second end is configured and adapted to receive an elongated member such as the K-wire. An elongated slot opening is provided in the elongated body extending longitudinally over a portion of the elongated body. A piston is provided within the bore and the piston is configured and adapted to travel in longitudinal direction within the bore. An elastically compressible member such as a coil spring is provided within the bore extending between the closed first end of the elongated body and the piston. On the outer surface of the elongated body, a graduated rule is provided along the elongated slot opening. An indicator connected to the piston through the elongated slot opening is also provided whereby when the elongated member such as a K-wire is inserted into the open second end of the elongated body, the elongated member urges the piston towards the closed first end of the elongated body compressing the elastically compressible member. As the piston moves along inside the bore, the indicator also moves along with the piston and indicates a value on the graduated rule. The elastically compressible member keeps the piston in contact with said elongated member.

BRIEF DESCRIPTION OF THE DRAWINGS

FIG. 1 is a perspective view of a drill guide assembly according to an embodiment of the present disclosure.

FIG. 2 is a plan view of the drill guide assembly of FIG. 1.

FIG. 3 is a side view of the drill guide assembly of FIG. 1.

FIG. 4 is an end view of the drill guide assembly of FIG. 1.

FIG. 4A is a detailed view of the region B in FIG. 4.

FIG. 5 is a perspective view of an example of a removable sleeve for use with the drill guide assembly of the present disclosure.

FIG. 6 is a side view of the removable sleeve of FIG. 5.

FIG. 7 is an end view of the removable sleeve of FIG. 5.

FIG. 8 is a top view of the removable sleeve of FIG. 5.

FIG. 9 is a cross-sectional view of the removable sleeve through the line A-A shown in FIG. 8.

FIG. 10 is a side view of the drill guide assembly of FIG. 1 with the removable sleeve of FIG. 5 inserted into the guide housing of the drill guide assembly.

FIG. 11 is a cross-sectional view of the guide housing and the removable sleeve assembly through the line A-A shown in FIG. 10.

FIG. 14B is a top view of the depth gage device of FIG. 14A.

FIG. 14C is a cross-sectional view of the depth gage device taken through the line A-A shown in FIG. 14B.

FIG. 14D is a detailed view of the area B identified in FIG. 14C.

FIG. 14E is a perspective view of an elastically compressible member 70 of the depth gage device of FIG. 14A.

FIG. 14F is a plan view of the depth gage device of FIG. 14A in use in conjunction with the drill guide assembly of FIG. 1.

FIG. 16 is a plan view of a drill guide assembly according to another embodiment of the present disclosure.

FIG. 17 is a cross-sectional view through the line C-C shown in FIG. 16.

FIG. 18 is a top view of the drill guide assembly of FIG. 16.

FIG. 19 is a cross-sectional view through the line A-A shown in FIG. 18.

FIG. 20 is a detailed view of the area B identified in FIG. 19.

The features shown in the above referenced drawings are illustrated schematically and are not intended to be drawn to scale nor are they intended to be shown in precise positional relationship. Like reference numbers indicate like elements.

DETAILED DESCRIPTION

Figure 1A:
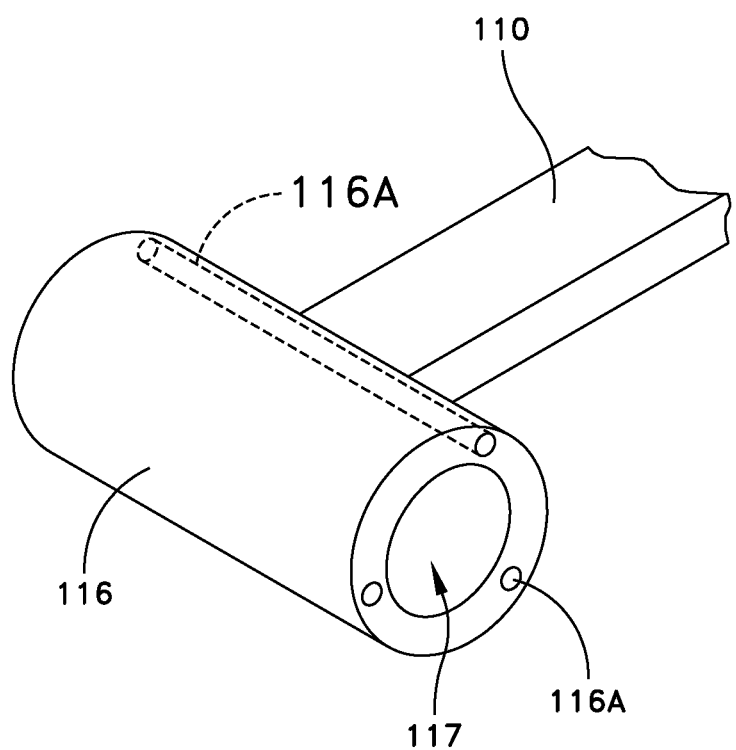
FIG. 1A is a perspective view of an embodiment of a guide housing.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

FIGS. 1-4 illustrate a drill guide assembly 100 according to an embodiment. The drill guide assembly 100 comprises an elongated body 102 having a first end 103A and a second end 103B. A first arm member 106 extends from the first end 103A of the elongated body 102. A modular second arm member 110 extends from the elongated body 102 and is configured and adapted to be longitudinally movable along the elongated body in two directions, towards or away from the first arm member 106. The second arm member 110 is referred to as being modular because it is formed from a piece separate from the elongated body 102. The second arm member 110 is provided with a guide housing 116 at its outer end (the end away from the elongated body 102). The guide housing 116 has a sleeve-receiving hole or a bore 117 for removably receiving a sleeve 20 (see FIGS. 5 and 10).

The lengths of the first arm member 106 and the second arm member 110 are matched so that the guide housing 116 and the tip 108 of the first arm member 106 align as shown. This alignment allows a K-wire or a drill bit inserted through the removable sleeve 20 positioned in the guide housing 116 to contact the tip 108 when the K-wire or the drill bit is extended towards the first arm member 106. This will be discussed further in connection with the various examples of surgical procedures for using the drill guide assembly. As shown in FIG. 2, an alignment notch 119 may be optionally provided on the tip 108 of the first arm member 106. The location of the alignment notch 119 is such that the longitudinal axis A of the guide housing 116 aligns with the alignment notch 119.

According to another embodiment, the guide housing 116 can be provided on the first arm member 106 rather than on the second arm member. In that embodiment, the outer end of the second arm member 110 would look like the tip 108 of the first arm member 106 shown in FIG. 1 and the alignment notch 119 would be provided on the second arm member 110.

The second arm member 110 has a base portion 112 that is configured and adapted to engage the elongated body 102 to allow the longitudinal movement of the second arm member 110 along the elongated body 102 towards and away from the first arm member 106. In one preferred embodiment, the elongated body 102 is four-sided having a generally rectilinear cross-section. The base portion 112 is provided with a matching rectilinear shaped through-hole 114 for receiving the elongated body 102. This arrangement prevents the second arm member 110 from rotating about the elongated body 102 and helps maintain the alignment between the first arm member 106 and the second arm member 110 discussed above.

As shown in FIGS. 3 and 4, in one preferred embodiment, one corner of the elongated body 102 is provided with a chamfer 102A so that the four-sided rectilinear cross-section of the elongated body 102 has a chamfered corner. FIG. 4A shows a detailed view of the region B in FIG. 4 with the body 102 of the drill guide assembly removed from the rectilinear shaped through-hole 114 of the base portion 112. The through-hole 114 is provided with a truncated corner 114A for aligning with the chamfer 102A of the body 102. The chamfer 102A provides the elongated body 102 with a lateral cross-sectional shape that is non-symmetric. This feature makes the assembly of the two modular components, the elongated body 102 and the second arm member 110, orientation sensitive. This feature ensures that the second arm member 110 is always in the correct orientation when the second arm member 110 is assembled with the body 102. The chamfer 102A functions as an orientation key. The orientation function can also be achieved with a variety of cross-sectional shapes for the elongated body 102 with or without a chamfer as long as the cross-sectional shape is asymmetric, such as a trapezoid. In the illustrated example, the lateral cross-sectional shape of the elongated body 102 and the corresponding through-hole 114 of the base portion 112 have rectilinear shape. However, other variations in the cross-sectional shape of the elongated body 102 that would provide the non-symmetry without substantially altering the other functions of the drill guide assembly is within the scope of the present disclosure.

The base portion 112 and the elongated body 102 are configured and adapted to operably engage each other so that the longitudinal movement of the second arm member 110 along the elongated body 102 is ratcheted. Ratchet teeth 104 are provided on one of the sides of the elongated body 102. The base portion 112 comprises a spring-loaded mechanism that cooperates with the ratchet teeth 104 and allows the second arm member 110 to be moved along the elongated body 102 in one direction, towards the first arm member 106, but prevents the second arm member 110 from backing out in the opposite direction, away from the first arm member 106. To move the second arm member 110 away from the first arm member 106, the spring-loaded mechanism must be unlocked. An example of the spring-loaded mechanism will be described in more detail in conjunction with FIG. 18.

Figure 12:
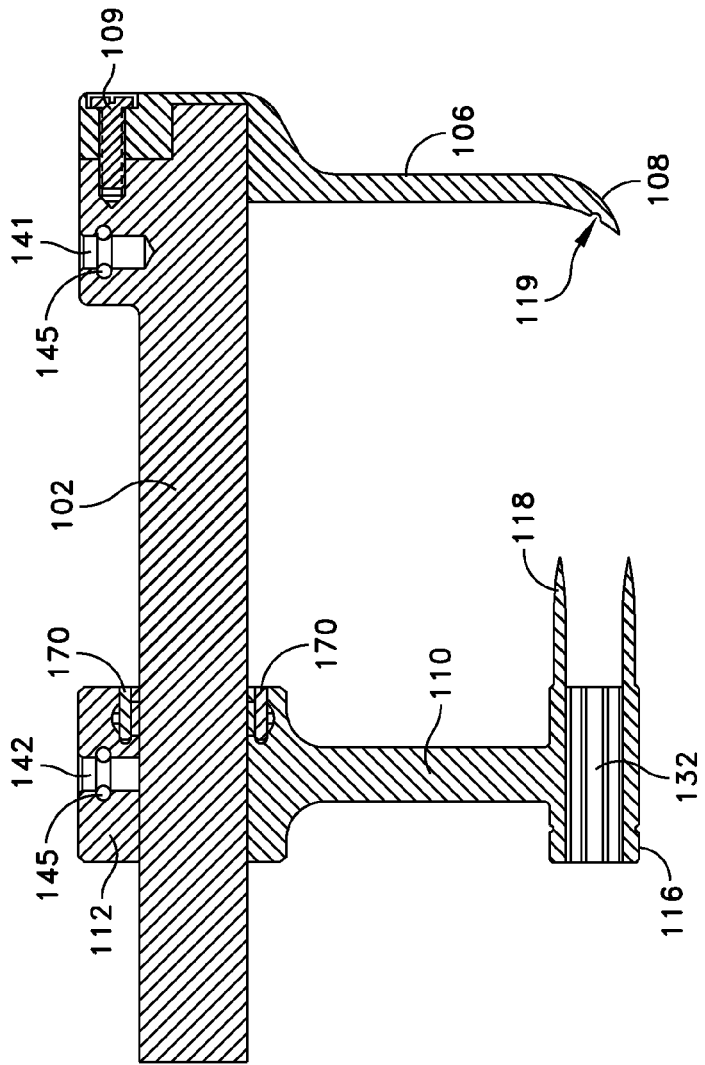
FIG. 12 is a cross-sectional view of the drill guide assembly of FIG. 1.

Because the drill guide assembly 100 is used to grasp a piece of bone or compress two or more pieces of soft tissues or bones between the two arm members in order to align and drill a hole for a bone screw, the guide housing 116 and the tip 108 of the first arm member 106 are configured and adapted to provide a good grip on the bone. In one embodiment, the tip 108 of the first arm member 106 terminates in a sharp point that can be used to penetrate the soft tissue covering the bone and also dig into the bone surface and help anchor the first arm member. The tip 108 can also be curved towards the second arm member 110 as shown in the embodiments of FIGS. 1, 10 and 12. This curvature allows the tip 108 to be wrapped around a bone if appropriate. On the guide housing 116, one or more spikes 118 can be provided on the side of the guide housing 116 facing the first arm member 106. The one or more spikes 118 extend longitudinally towards the first arm member 106 and terminate in a sharp point to dig into the bone surface and/or soft tissues. The length and number of the spikes 118 provided on a particular drill guide assembly can be varied to meet the requirements of the particular intended application. Preferably, the one or more spikes 118 are positioned on the guide housing 116 so that the spike(s) do not interfere with the K-wire or the drill bit that would be inserted through the guide housing 116.

Referring to FIG. 1A, according to another embodiment, the guide housing 116 can be provided with one or more holes 116a for fixating the instrument to a bone using K-wires or screws. The holes 116a preferably extend through the guide housing 116 longitudinally.

During actual use, an external imaging method will generally be used to verify the position and alignment of the drill guide assembly with respect to the bone. External imaging method can include currently available technologies such as X-ray radiography, fluoroscopy, etc. and yet to be developed external imaging technologies. To enable this verification by external imaging such as X-ray radiography and fluoroscopy, in one preferred embodiment, the elongated body 102 of the drill guide assembly is made from a radiolucent material. One example of such material suitable for this application is polyetheretherketone (PEEK) thermoplastic polymer. Glass filled PEEK and carbon filled PEEK are some examples. When such polymer is used for the body 102, the body 102 must have appropriate thickness so that the body 102 has sufficient stiffness. Aluminum alloys can also be radiolucent if it is thin enough. The first arm member 106 can also be radiolucent but in one preferred embodiment, at least the tip portion 108 of the first arm member 106 is made to be radiopaque (i.e. made of metal) so that the tip 108, the guide housing 116 and the K-wire, for example, are visible in X-ray radiography in order to properly verify and confirm the alignment of the K-wire and the position of the drill guide. In an embodiment where the first arm member 106 is made of a metal and the elongated body 102 is made of a radiolucent polymer, the first arm member 106 would be mechanically joined to the body. For example, in the embodiment shown in FIG. 12, the first arm member 106 is joined to the body 102 by a screw 109.

FIGS. 5-9 illustrate an example of the sleeve 20 for removably inserting into the guide housing 116 of the drill guide assembly 100. The sleeve 20 has a generally cylindrical body 21 that is inserted into the sleeve-receiving hole 117. The sleeve 20 has a central bore 23 longitudinally extending through the full length of the sleeve 20. The bore 23 is centrally located in the sleeve 20 such that when the sleeve 20 is inserted into the guide housing 116, the longitudinal or central axis of the bore 23 coincides with the longitudinal axis A of the guide housing 116. If the sleeve 20 is a K-wire sleeve used to guide a K-wire, the diameter of the bore 23 is matched to that of the particular K-wire. If the sleeve 20 is a drill sleeve used to guide a drill bit, the diameter of the bore 23 is matched to that of the particular drill bit. In one preferred embodiment, the sleeve 20 is provided with a flared head portion 22 at the top end that can act as a stop when the sleeve 20 is inserted into the guide housing 116.

The sleeve 20 can also have a retention tab 24 extending downward from the flared head portion 22 that cooperates with the guide housing 116 for retaining the sleeve 20 in place and prevent the sleeve 20 from falling or sliding out of the guide housing 116. As illustrated in FIGS. 6, 8 and 9, the retention tab 24 is provided with a spring-loaded detent 27 that protrudes from the inner surface 25 of the retention tab 24. The spring-loaded detent 27 urges against the guide housing 116 and retains the sleeve in place. The detent 27 can be spring-loaded inside the retention tab 24 as shown in the detailed view of FIG. 9. The spring-loaded detent 27 and a compressible member 28 such as a coil spring and steel ball are held within a cavity 26 by a set screw 29.

In one preferred embodiment, an annular groove 115 is provided on the outer surface of the guide housing 116 to cooperate with the spring-loaded detent 27 as shown in FIGS. 1 and 2. The groove 115 is referred to as an annular groove because it forms a ring around the outer surface of the guide housing 116. When the sleeve 20 is fully inserted into the guide housing 116, the spring-loaded detent 27 is extended into the groove 115 and prevents the sleeve 20 from unintentionally falling out of the guide housing 116. This arrangement is shown in the assembled views of FIGS. 10 and 11. The sleeve 20 can be removed by simply pulling it out using some force to compress the spring-loaded detent 27. In other embodiments, the groove 115 can be replaced with other structures such as indentations that will provide the same function as the groove 115 of receiving the spring-loaded detent 27.

Figure 13:
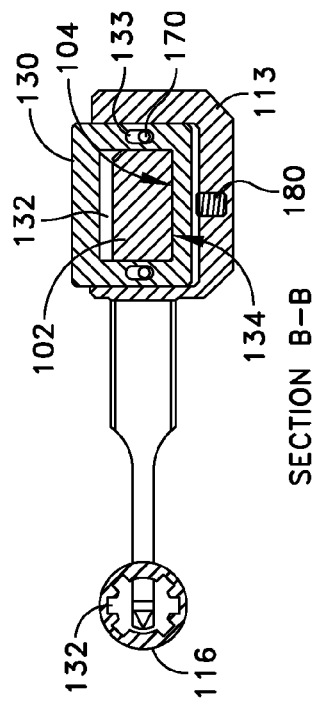
FIG. 13 is a cross-sectional view of the drill guide assembly of FIG. 1 through the line B-B shown in FIG. 3.

Referring to FIGS. 12 and 13, in another example, the guide housing 116 and the sleeve 20 can be configured and adapted to prevent the sleeve 20 from rotating within the guide housing 116. The sleeve 20 can be provided with an alignment tab 32 on its outer surface of the sleeve body 21 and the guide housing 116 can be provided with corresponding grooves 132 running longitudinally along the inner surface of the sleeve-receiving hole 117.

FIG. 13 is an illustration of a cross-section taken through the ratchet engaging portion 113 of the base 112 of the second arm member 110 showing the details of an example of a ratcheting mechanism between the second arm member 110 and the elongated body 102. The elongated body 102 of the drill guide 100 extends through the base 112 as shown. Inside the ratchet engaging portion 113, a button 130 having a through hole 134 for accommodating the elongated body 102 is provided. The button 130 is configured to move up and down in perpendicular direction to the ratchet teeth 104 surface of the elongated body 102. In this example, slots 133 in the button 130 cooperate with the button guide pins 170 to limit the up and down travel of the button within the ratchet engaging portion 113. A top side 130A of the button 130 is exposed and protrudes from the ratchet engaging portion 113.

The bottom side 130B of the button resides within the ratchet engaging portion 113 and a coil spring 180 positioned between the button 130 and the ratchet engaging portion 113 urges against the bottom side 130B of the button. This keeps the bottom surface (in the orientation shown in FIG. 13) of the through hole 134 pushed up against the ratchet teeth 104 when in a resting position. The ratchet teeth 104 are oriented in one direction such that when the second arm member 110 is pushed towards the first arm member 106, the button 130 will slide over the ratchet teeth 104 while preventing the second arm member 110 to be moved away from the first arm member 106. To move the second arm member 110 away from the first arm member 106, the button 130 has to be pressed down (in the orientation shown in FIG. 13) thus disengaging the button 130 from the ratchet teeth 104. The structure described herein is just one example of a ratcheting mechanism that can be implemented to engage the base 112 of the second arm member 110 to the elongated body 102 of the drill guide assembly.

Referring to FIGS. 14A-14F, a depth gage 60 for use in conjunction with the drill guide of the present disclosure will be described. The depth gage 60 is used to measure the depth of the K-wire 400 (see FIG. 14F) drilled into the bone to determine the proper length of the bone screw. After the K-wire 400 is drilled into the bone with the drill guide in place, the depth gage 60 is slid over the remaining portion of the K-wire 400 that is not drilled into the bone and the depth gage 60 readily tells the surgeon the depth of the K-wire's penetration into the bone.

In one embodiment, the depth gage 60 comprises a hollow elongated body 61 having an opening at one end 63 for receiving an elongated member, the K-wire 400 having a length. A spring-loaded piston 72 is provided within the hollow elongated body 61 for urging against the K-wire 400 received in the opening at one end 63 of the hollow elongated body. When the K-wire 400 is received into the opening and pushes the spring-loaded piston 72 away from the opening, the distance traveled by the spring-loaded piston 72 provides an indication about the length of the K-wire 400. Specifically, in the application described herein, by sliding the depth gage 60 over the K-wire until the leading end 63 of the depth gage 60 contacts the bone surface, the distance traveled by the spring-loaded piston 72 indicates the length of the portion of the K-wire 400 that is drilled into the bone. Thus the depth of the bone drilled by the K-wire 400 is measured.

Figure 14A:
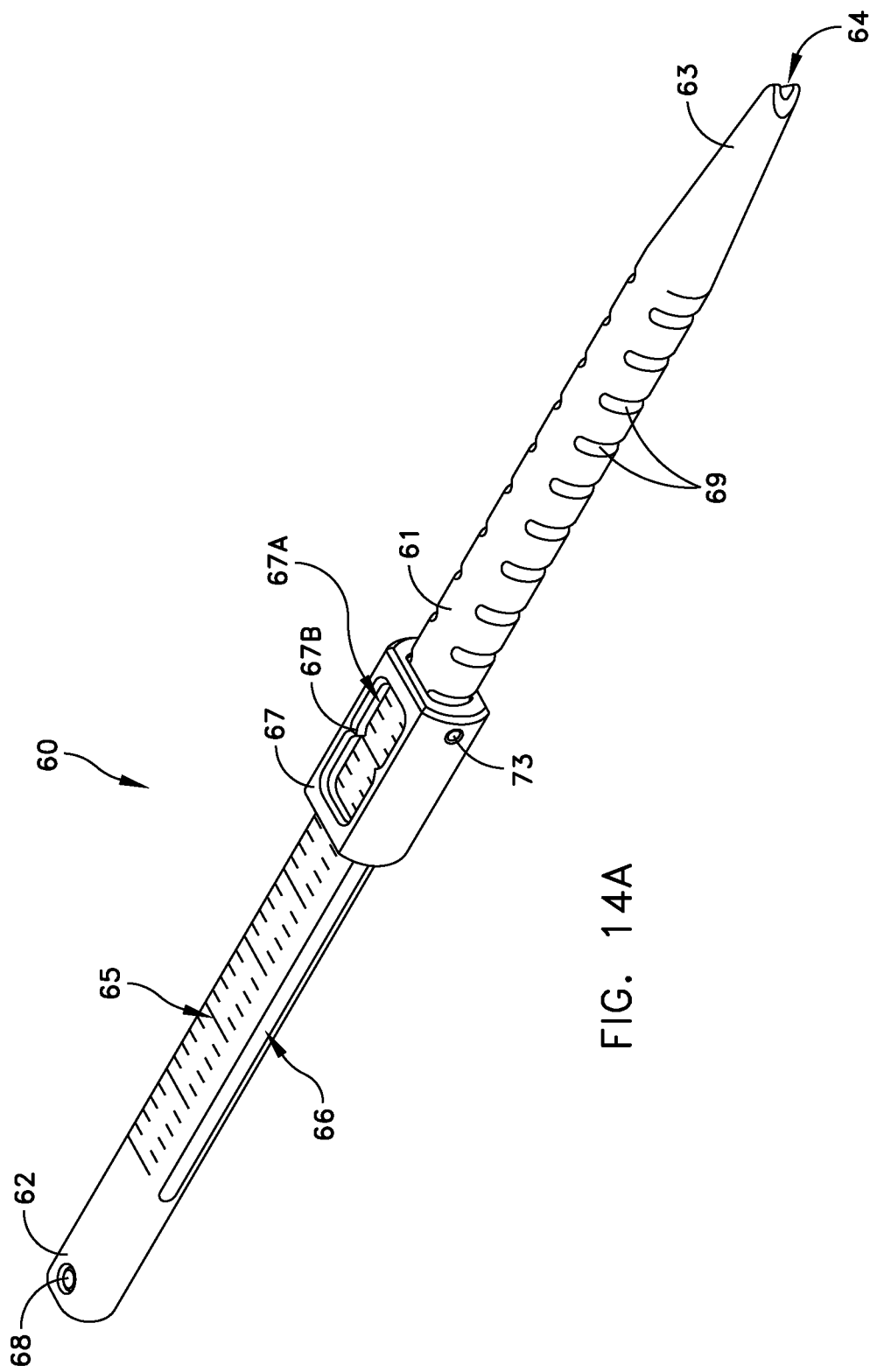
FIG. 14A is a perspective view of a depth gage device according to an aspect of the present disclosure.

In another embodiment, the depth gage 60 comprises a cannulated elongated body 61 having a first end 62 and a second end 63 and a bore 64 longitudinally extending through the length of the elongated body 61. The bore 64 is closed at the first end 62 of the elongated body and open at the second end 63 of the elongated body, the open second end 63 being configured and adapted to receive an elongated member such as a K-wire. A pair of elongated slot openings 66 are provided in the elongated body diametrically opposed from one another and extend longitudinally over a portion of the elongated body 61. FIG. 14A shown one of the two through slots 66 on the near-side of the depth gage 60. The other slot opening would be on the opposite side of the depth gage 60, the side not visible in the FIG. 14A view.

A piston 72 is provided within the bore 64 and is configured to travel in longitudinal direction within the bore. An elastically compressible member 70 is also provided within the bore 64 and extends between the closed first end 62 of the elongated body and the piston 72. The piston 72 and the compressible member 70 can be attached to one another but this is not necessary. As shown in FIG. 14E, the piston 72 can be provided with a pair of guide pins 73. The guide pins 73 extend into the slot openings 66 for guiding the piston as it is slides longitudinally within the bore 64. The guide pins 73 can be a single pin that is placed through the piston 72 as shown in FIG. 14E.

At the first end 62 of the depth gage, the bore 64 is closed off to prevent the elastically compressible member 70 from falling out through that end. The bore 64 can be closed off in a variety of possible ways. In one example shown in FIGS. 14A-14C, a stopping pin 68 placed through the body 61 of the depth gage 60 blocks the first end 62.

A graduated rule 65 is provided on the outer surface of the elongated body along said elongated slot opening 66. In the embodiment of the depth gage 60 shown in FIG. 14A, the graduated rule 65 is provided on a flat surface of the elongate body 61.

A sliding indicator 67 is provided for reading the measurement from the graduated rule 65 which indicates the length of an elongated member such as a K-wire that is drilled into the bone. The sliding indicator 67 is configured and adapted to cooperate with the piston 72 to move along with the piston 72 as the piston 72 moves inside the bore 64. The sliding indicator 67 can be connected to the piston 72 by the guide pins 73 as shown in FIG. 14A. The guide pin 73 is fitted through holes in the sliding indicator 67. The guide pin 73 extends from one side of the sliding indicator 67 through the slot openings 66 and the piston 72 and out to the other side of the sliding indicator 67, thus, connecting the sliding indicator 67 to the piston 72 residing within the bore 64. As the piston moves up and down within the bore 64, the sliding indicator 67 follows along from the outside of the depth gage 60. The sliding indicator 67 can be provided with at least one marker 67B for indicating a reading along the graduated rule 65. In the particular embodiment shown in FIG. 14A, the sliding indicator 67 is provided with a window 67A and a pair of markers 67B are provided to indicate the measurement on the graduated rule 65 shown through the window 67A.

The bore 64 can be defined into two portions, a front portion 64A and a back portion 64B. The front portion 64A is where an elongated member, such as a K-wire, is received for measurement and the inside diameter of the front portion 64A is appropriately matched to the diameter of the intended elongated member. The back portion 64B is where the elastically compressible member 70 and the piston 72 reside. Thus, the inside diameter of the back portion 64B is appropriately matched to the diameter of the elastically compressible member 70 and the piston 72. Where the diameter of the elastically compressible member 70 and the piston 72 are larger than the diameter of the front portion 64A, the inside diameter of the back portion 64B will be larger and there will be a transition portion 64C where the diameters change. (See FIG. 14D). The transition portion 64C can act as a stop for the piston 72 defining its resting position.

As discussed above during the description of the surgical procedures, after a K-wire is drilled into a bone to a certain depth using the drill guide, the depth gage 60 can be used to measure the length of the K-wire that is inside the bone. This measurement is necessary to determine the proper length of a bone screw that will be used after the K-wire is removed and a hole is drilled into the bone.

As shown in FIG. 14F, to measure the depth of the K-wire 400 inside the bone pieces 501 and 502, the open end of the depth gage 60 at the second end 63 is slid over the portion of the K-wire that is remaining outside the bone until the leading tip of the depth gage 60 contacts the bone. The K-wire 400 extends into the bore 64 contacts the piston 72 and pushes the piston 72 back until the depth gage 60 contacts the bone surface and cannot be advanced further. The elastically compressible member 70, which can be a coil spring or some other suitable component, urges the piston 72 against the K-wire and helps the piston 72 constantly maintain the contact with the K-wire 400. This feature allows the depth gage 60 to be used accurately and easily in any orientation.

Because the overall length of the K-wire 400 is known and the distance from the leading tip of the depth gage 60 to the resting position of the piston 72 is also known, the graduated rule 65 can be calibrated to provide the length of the portion of the K-wire that is drilled into the bone. Alternatively, the graduated rule 65 can be calibrated to provide the length of the K-wire that is remaining outside the bone in which case the surgeon can subtract that figure from the known total length of the K-wire to determine the length of the K-wire that is drilled into the bone.

Figure 14G:
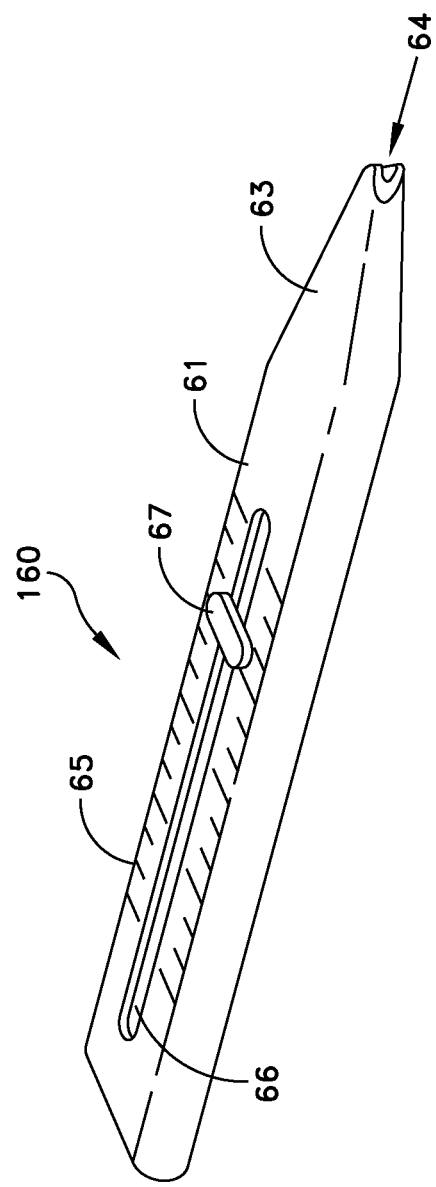
FIG. 14G is a perspective view of another embodiment of the depth gage device.

FIG. 14G shows a depth gage 160 according to another embodiment. The depth gage 160 functions the same way as the depth gage 60 shown in FIG. 14A. The depth gage body 61 is provided with a longitudinally extending bore 64. To measure the depth of a K-wire, the front end 63 of the depth gage is slipped over the K-wire portion that remains outside a bone. Inside the depth gage 60 is provided with the piston 72 and the elastically compressible member 70. The piston's sliding movement within the depth gage 160 is guided by the slot opening 66. The slot opening is oriented in longitudinal direction and a graduated rule 65 is provided along the slot opening 66. But unlike in the depth gage 60, in this embodiment, the slot opening 66 and the graduated rule 65 are on the same side of the body 61. The sliding indicator 67 connected to the piston 72 via the guide pin 73 (not visible in FIG. 14G) moves along the graduated rule following the piston's movement and thus indicating a measurement that correlates with the length of the K-wire drilled into the bone pieces.

Figure 15:
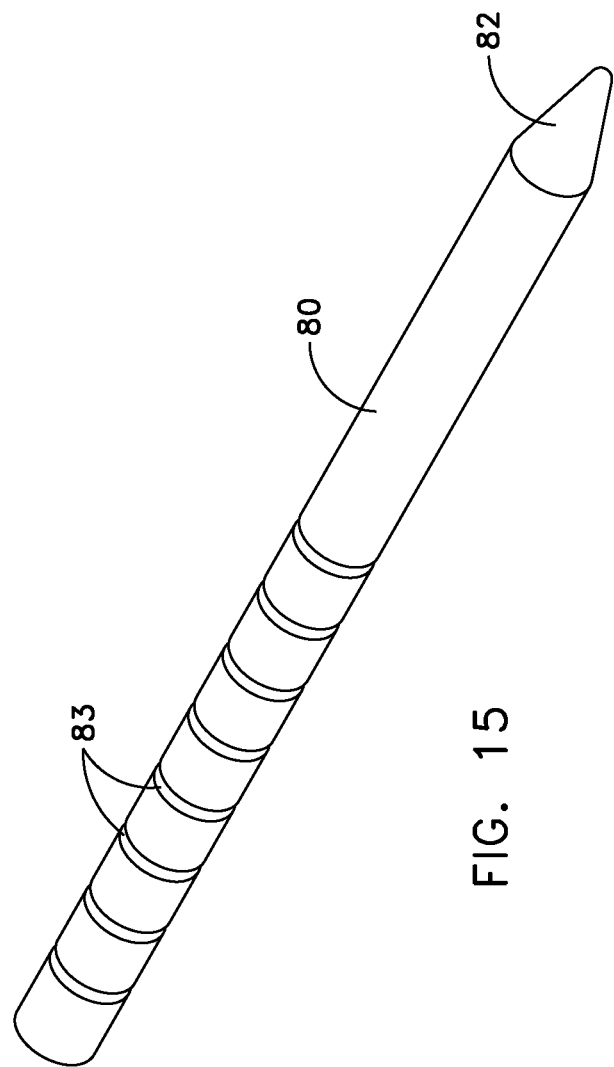
FIG. 15 is a perspective view of a blunt trocar that can be used in conjunction with the drill guide assembly of the present disclosure.
Figure 21:
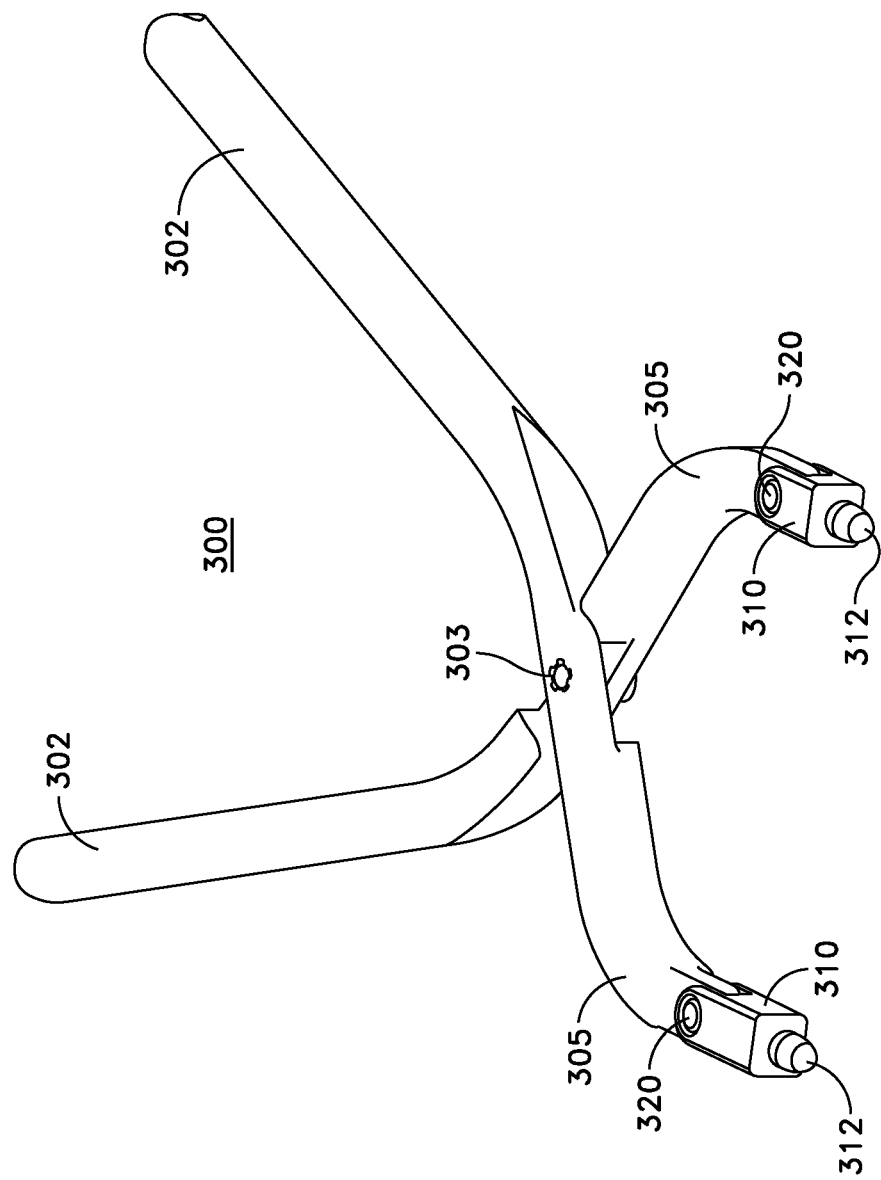
FIG. 21 is a perspective view of a handle for use in conjunction with the drill guide assembly of the present disclosure.
Figure 22:
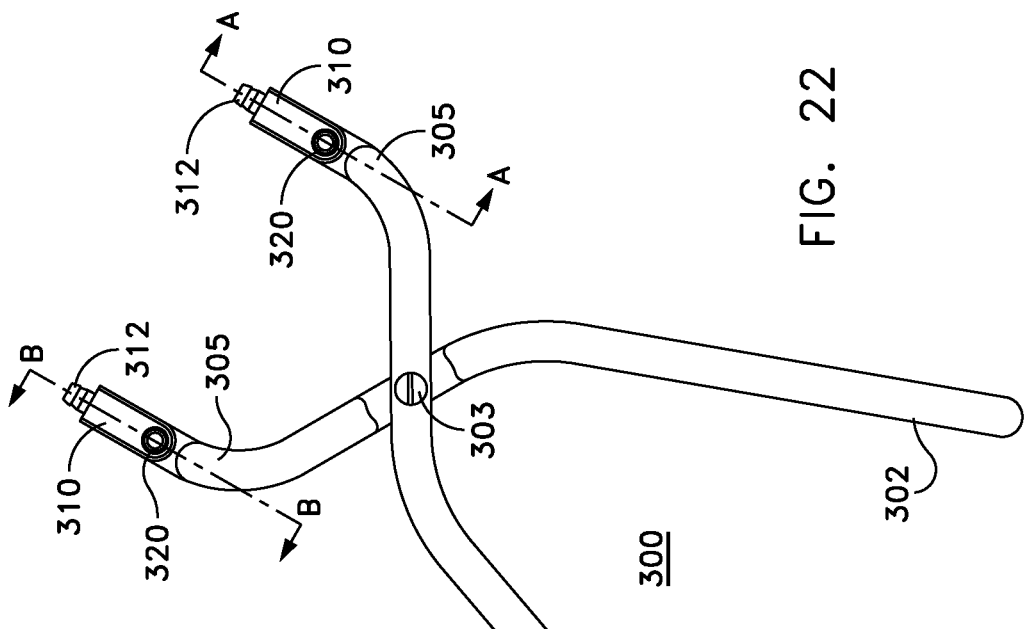
FIG. 22 is a plan view of the handle of FIG. 21.

FIG. 15 shows a blunt trocar 80 for use with the drill guide assembly. The blunt trocar 80 can be used in conjunction with the drill-guiding sleeve 20 to verify the entry point for the drill. The trocar 80 comprises a blunt tip 82 and a plurality of grooves 83 can be provided on the body of the trocar to enhance gripping by the user. After the drill guide assembly is secured into a desired position around a repair site, the blunt trocar 80 can be inserted into the drill-guiding sleeve 20 and advanced until the blunt tip 82 contacts the surface to be drilled. The point of contact represents the drill entry point. Then, X-ray can be used to verify that the location of the drill entry point is correct. Alternatively, the blunt trocar 80 can have a diameter that is same as the outer diameter of the sleeve 20 in which case, the blunt trocar 80 can fit directly into the guide housing 116 and can be used without the drill-guiding sleeve 20.

FIGS. 16-20 show a drill guide assembly 200 according to another embodiment. In this embodiment, the one or more spikes 118 are provided on a base member 220, the base member 220 configured and adapted to rotatably engage the guide housing 116. FIG. 17 shows the detailed structure of the spike base member 220. The base member 220 circumscribes the end of the guide housing 116 that is closer to the first arm member 106 and is rotatable about the longitudinal axis of the guide housing 116. The base member 220 is rotated to adjust the location of the one or more spikes 118. The base member 220 is provided with a hole 223 that aligns with the sleeve-receiving hole 117 of the guide housing 116. The base member 220 is also provided with means for securing the base member onto the guide housing 116. For example, in the embodiment shown in FIG. 17, one or more set screws 222 are tapped into the side of the base member 220 to hold the base member 220 in place. The guide housing 116 is provided with a groove or indentations to cooperate with the set screws 222.

The base member 220 can be locked in place by tightening the set screws 222. Optionally, by adjusting the set screws 222, the base member 220 can be allowed to freely rotate without disengaging from the guide housing 116. In another example, spring-loaded detents and pins can be provided in place of the set screws 222. The spring-loaded detents and pins would also allow the base member 220 to freely rotate without disengaging from the guide housing 116. As shown in FIG. 19, the outer surface of the base member 220 can be provided with a plurality of tabs 224 to help with turning the base member 220. FIG. 20 shows the same ratcheting mechanism structure shown in FIG. 13 and described in conjunction with the drill guide assembly 100.

FIGS. 21-25 show an example of a clamp 300 that can be used to assist in the bone reduction using the drill guide assemblies of the present disclosure. The clamp 300 is generally constructed like a pair of pliers and comprises handles 302 connected by a hinge 303. The operable ends 305 of the clamp 300 are configured to engage the drill guide assemblies 100, 200 to assist compressing the first and second arm members 106 and 110 together for bone reduction.

Figure 25:
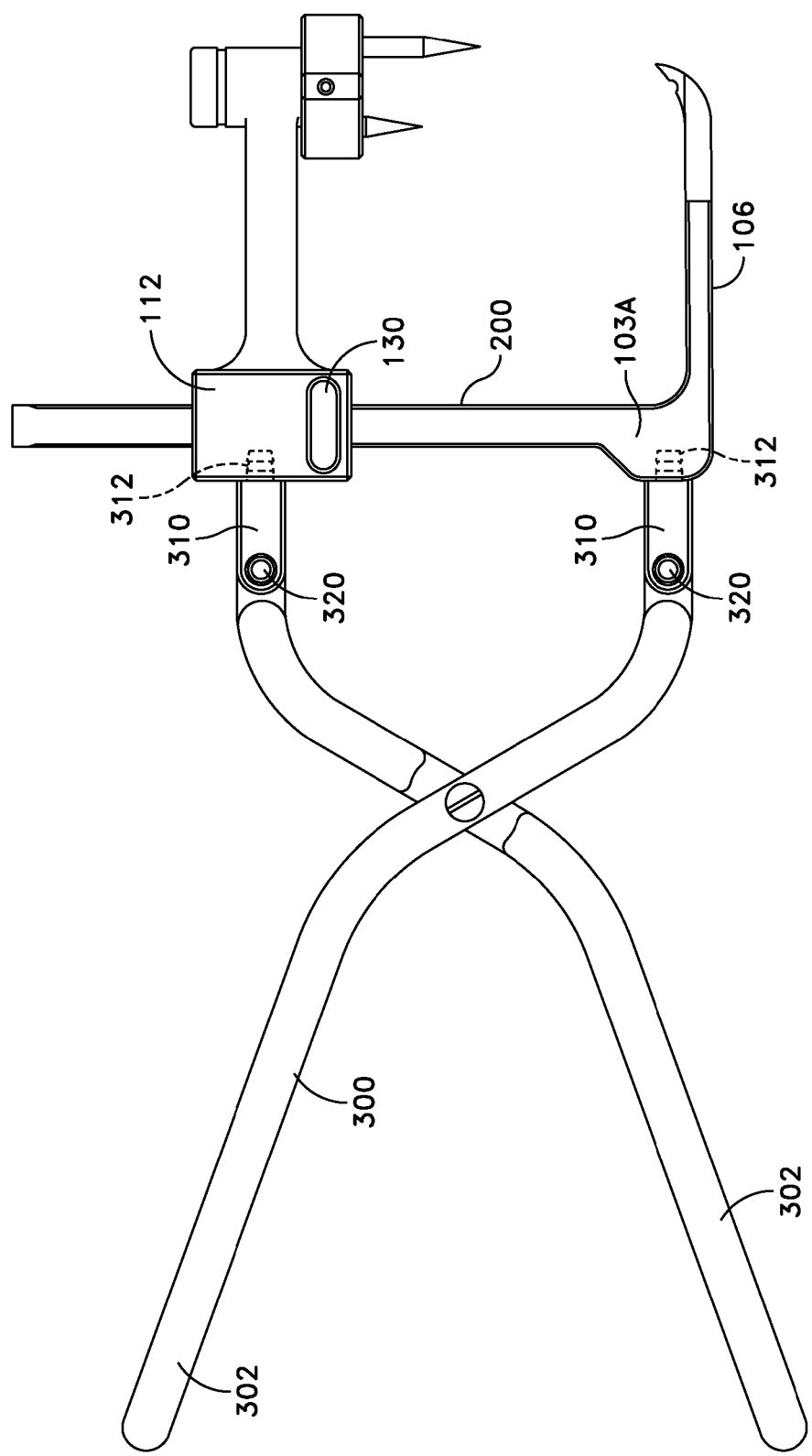
FIG. 25 is a side view of the clamp of FIGS. 16 and 21 operably engaged with the drill guide assembly of the present disclosure.

Referring to FIGS. 3, 12 and 18, the drill guide assemblies 100 and 200 are provided with clamp engaging holes 141, 142. The first hole 141 is provided near the first end 103A of the elongated body 102. The second hole 142 is provided on the base 112 of the second arm member 110. Each of the two operable ends 305 of the clamp 300 are provided with a pin 312. The pins 312 are inserted into the holes 141 and 142 of the drill guide assembly as shown in FIG. 25. Closing the handles 302 will compress the second arm member 110 towards the first arm member 106.

Figure 23:
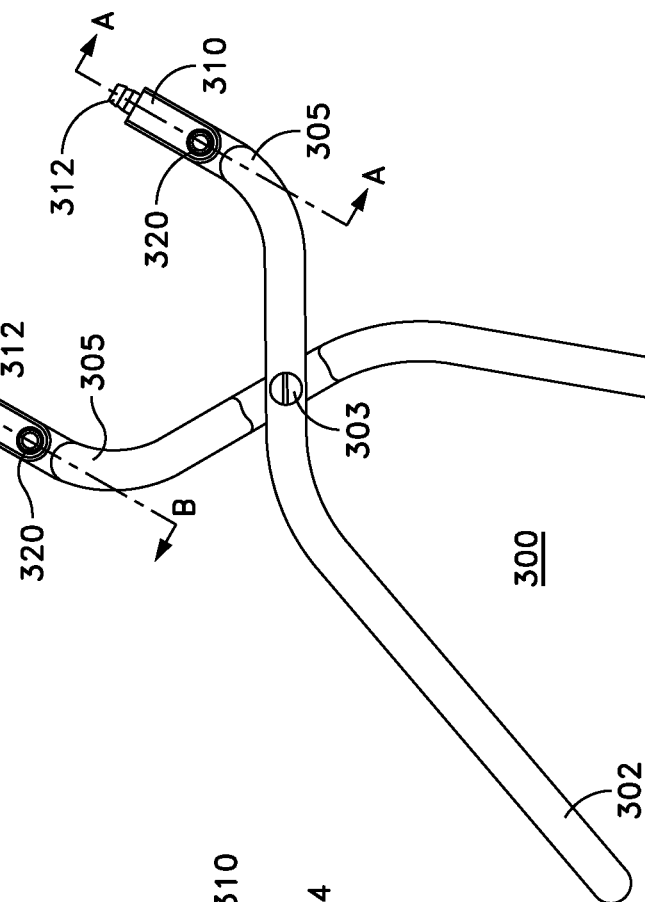
FIGS. 23 and 24 are cross-sectional views taken through the lines A-A and B-B shown in FIG. 22, respectively.
Figure 24:
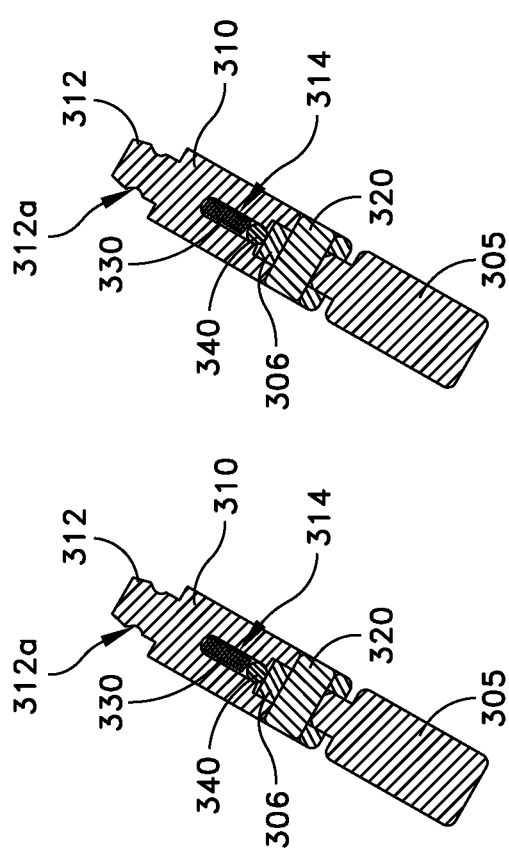

In one preferred embodiment, the operable ends 305 are configured to have an articulated end 310 that pivots about the hinge 320. The detailed cross-sectional views of the articulated ends 310 in FIGS. 23 and 24 show that a spring loaded ball 340 can be provided between the articulated ends 310 and the operable ends 305 to register the articulated ends 310 into certain predefined positions. This can be helpful in inserting the pins 312 into the receiving holes 141, 142 by keeping the articulated joint somewhat rigid. A coil spring 330 and the ball 340 can be provided within a chamber 314 inside the articulated end 310. The operable ends 305 can be provided with terminal ends 306 that engage the ball 340 to register the position of the articulated ends 310. The terminal ends 306 can be configured with one or more indents to register ball 340 as the articulated ends 310 are pivoted.

Referring to FIG. 12, each of the clamp engaging holes 141 and 142 can be provided with a locking ring 145 that will cooperate with grooves 312a (see FIGS. 23 and 24) on the pins 312 to lock the clamp 300 into the holes 141 and 142 to prevent the clamp 300 from disengaging from the drill guide assembly unintentionally.

Figure 28:
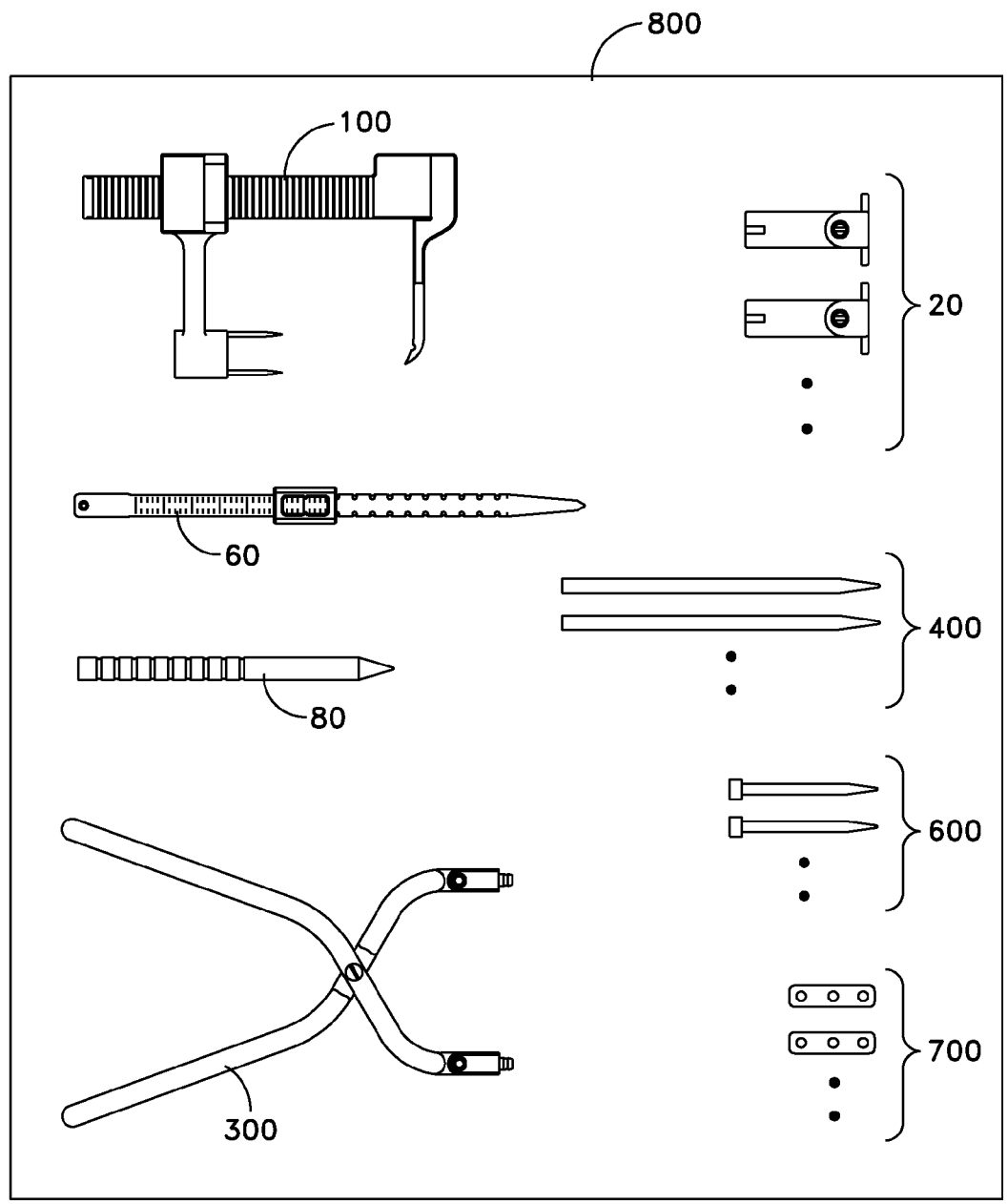
FIG. 28 is a schematic illustration of a surgical drill guide kit including the drill guide assembly of the present disclosure.

Referring to FIG. 28, in another embodiment, the drill guide assembly 100 can be provided as part of a surgical drill guide kit 800 containing all necessary accessories and parts. One embodiment of a surgical drill guide kit comprises the drill guide assembly 100, one or more sleeves 20 (some of which can comprise K-wire guiding sleeves for receiving various sizes of K-wires and drill-guiding sleeves for receiving various sizes of drill bits), one or more K-wires 400 of varying sizes, one or more bone screws 600 of varying sizes, a depth gage 60, a blunt trocar 80, and a clamp 300. The surgical drill guide kit 800 can also include other implants such as one or more bone plates 700 of appropriate sizes and configurations. The components of the kit 800 are preferably arranged in a convenient format, such as a surgical tray or a case. However, the kit components do not have to be packaged or delivered together, provided that they are assembled or collected together in the operating room for use at the time of surgery.

According to another aspect of the present disclosure, an example of a surgical procedure for using the disclosed drill guide assembly will be described. An example of such surgical procedure is aligning and drilling a hole for a bone screw to repair fractured bones or secure two adjacent bones to repair damaged soft tissues (e.g. ligaments) in the mid-foot region, such as a Lisfranc foot injury.

Figure 26:
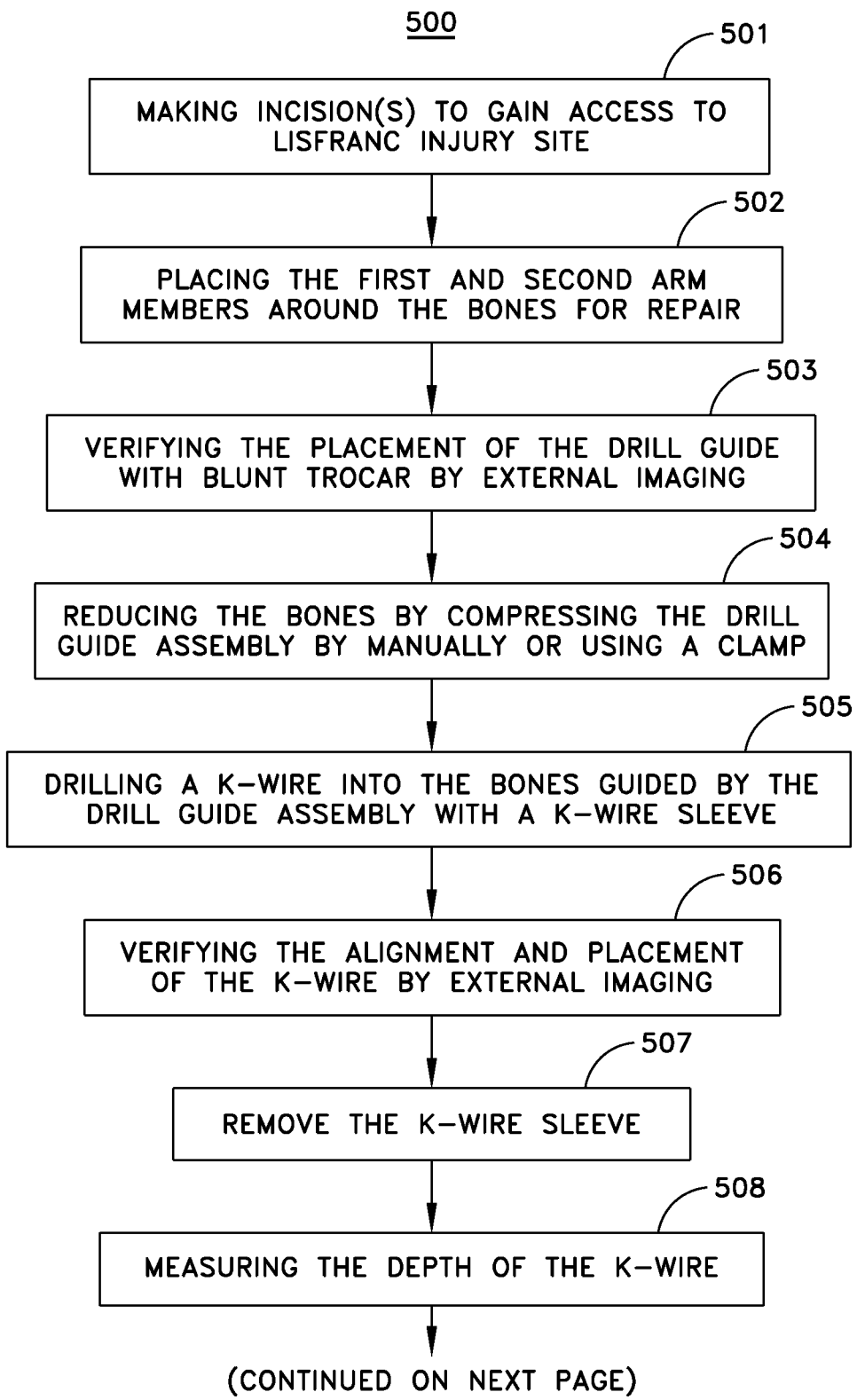
FIG. 26 is a flowchart of the method according to one embodiment of the present disclosure.
Figure 26:
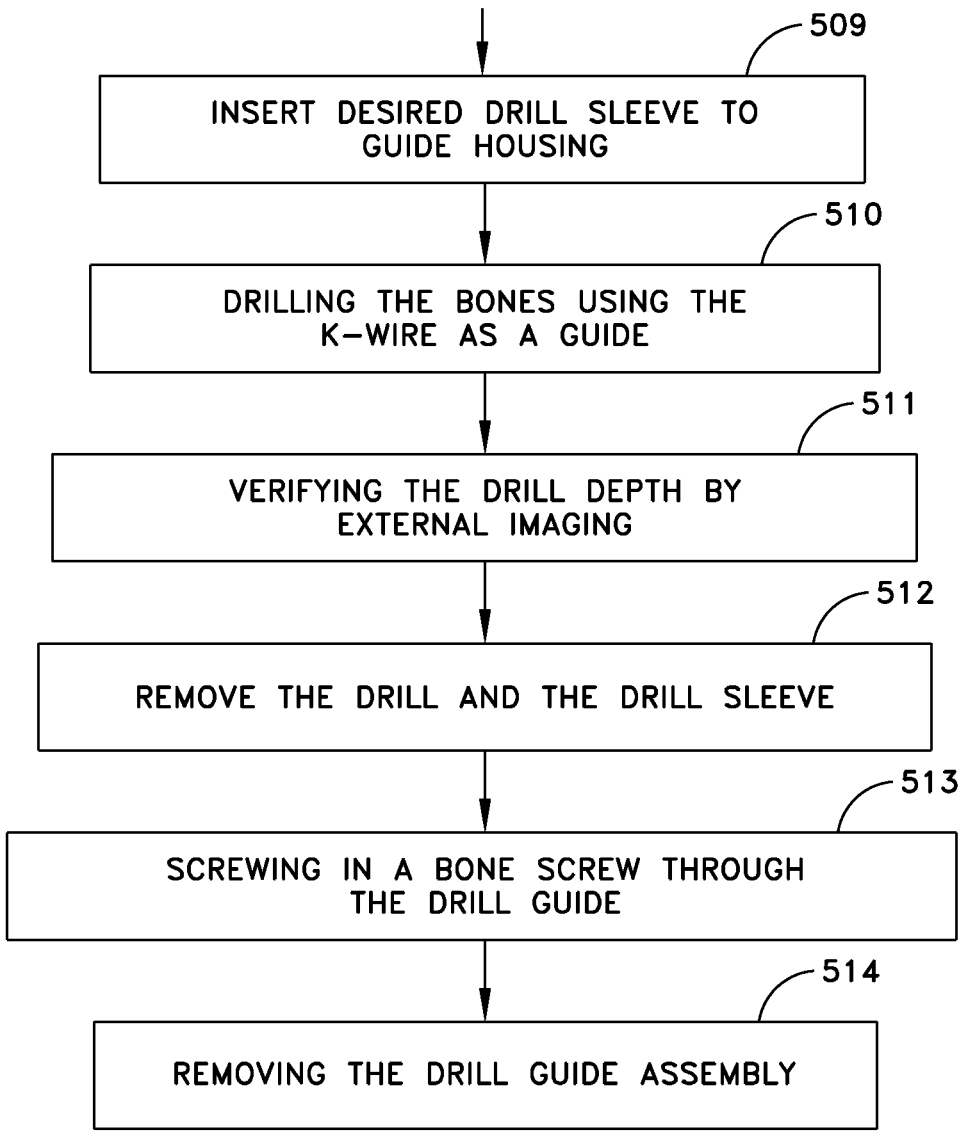

An embodiment of the procedure for repairing a Lisfranc foot injury will be described referring to FIG. 26 and FIGS. 27A-27F. FIG. 26 shows a flowchart 500 of the method described herein. [Exposure/Joint Preparation]—Depending on the degree of injury and instability, one or two dorsal longitudinal incisions are made to gain access to the injury site (see FIG. 27A and block 501 of FIG. 26). The first incision is made between the first and second metatarsal bases (FIG. 27A) and the second incision is made parallel to the first between the third and fourth metatarsal bases. Care should be taken to protect the sensory branches of the superficial peroneal nerve. Typically a small avulsion fracture can be seen at the medial base of the second metatarsal where the Lisfranc ligament attaches. Any small free pieces of cartilage should be removed and joint surfaces debrided if arthrodesis is desired.

[Reduction]—The drill guide assembly 100 is used to maintain the reduction between the second metatarsal and the medial cuneiform. The first and second arm members 106, 110 of the drill guide assembly are placed around the second metatarsal and the medial cuneiform. Specifically, the hook-shaped tip portion 108 of the first arm member 106 is placed between the second and third metatarsal base. The targeting area (drilling point) placement on the medial cuneiform is determined using the spike 118 component of the second arm member 110 before fully reducing the Lisfranc joint. The targeting of the drilling point is done by moving the second arm member 110 towards the first arm member 116 until the spike 118 is placed on the medial side of the medial cuneiform in the general location where the bone is to be drilled (see FIG. 27B and block 502 of FIG. 26). Next, the placement of the drill guide assembly 100 can be optionally verified by using the blunt trocar 80 and an external imaging as described above and adjusted if necessary (see block 503 of FIG. 26). Once the placement of the drill guide assembly 100 is finalized, the drill guide assembly 100 is used to reduce the Lisfranc joint by closing the two arm members 106, 110 together (see block 504 of FIG. 26). Generally, this compression can be done by hand and the ratcheting mechanism of the second arm member 110 aids in achieving the desired reduction of the bones. If necessary, however, additional compression force may be gained by the use of the clamp 300.

Figure 27A:
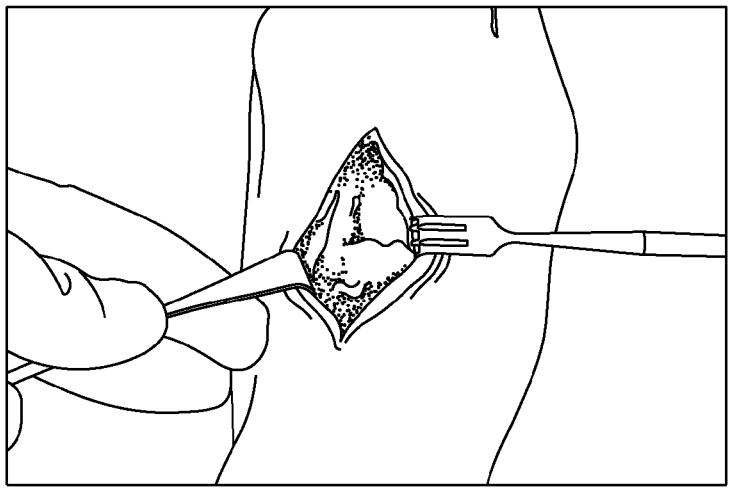
FIGS. 27A-27F are photographs illustrating the various interim steps of the method of FIG. 26.
Figure 27B:
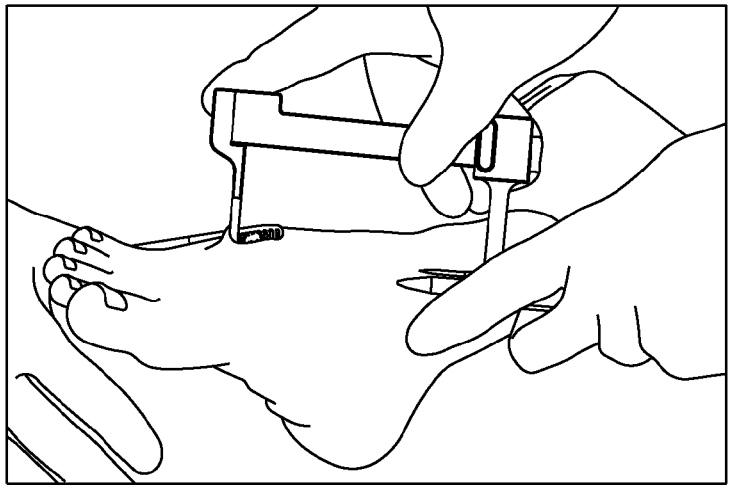
Figure 27C:
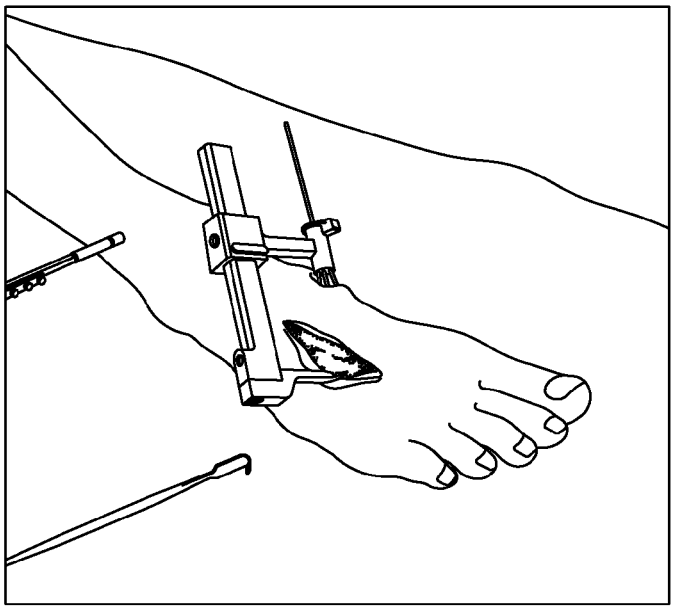

[K-wire placement]—Next, a K-wire guiding sleeve 20 is inserted into the guide housing 116 and a 1.6 mm K-wire is inserted into the sleeve's bore 23 and drilled through the medial cuneiform and the second metatarsal until an external imaging shows the K-wire touching the tip 108 of the first arm member 106 on the lateral side of the second metatarsal (see FIG. 27C and block 505 of FIG. 26). Preferably, the position of the K-wire is verified by an external imaging in AP and lateral views (see block 506 of FIG. 26).

Figure 27D:
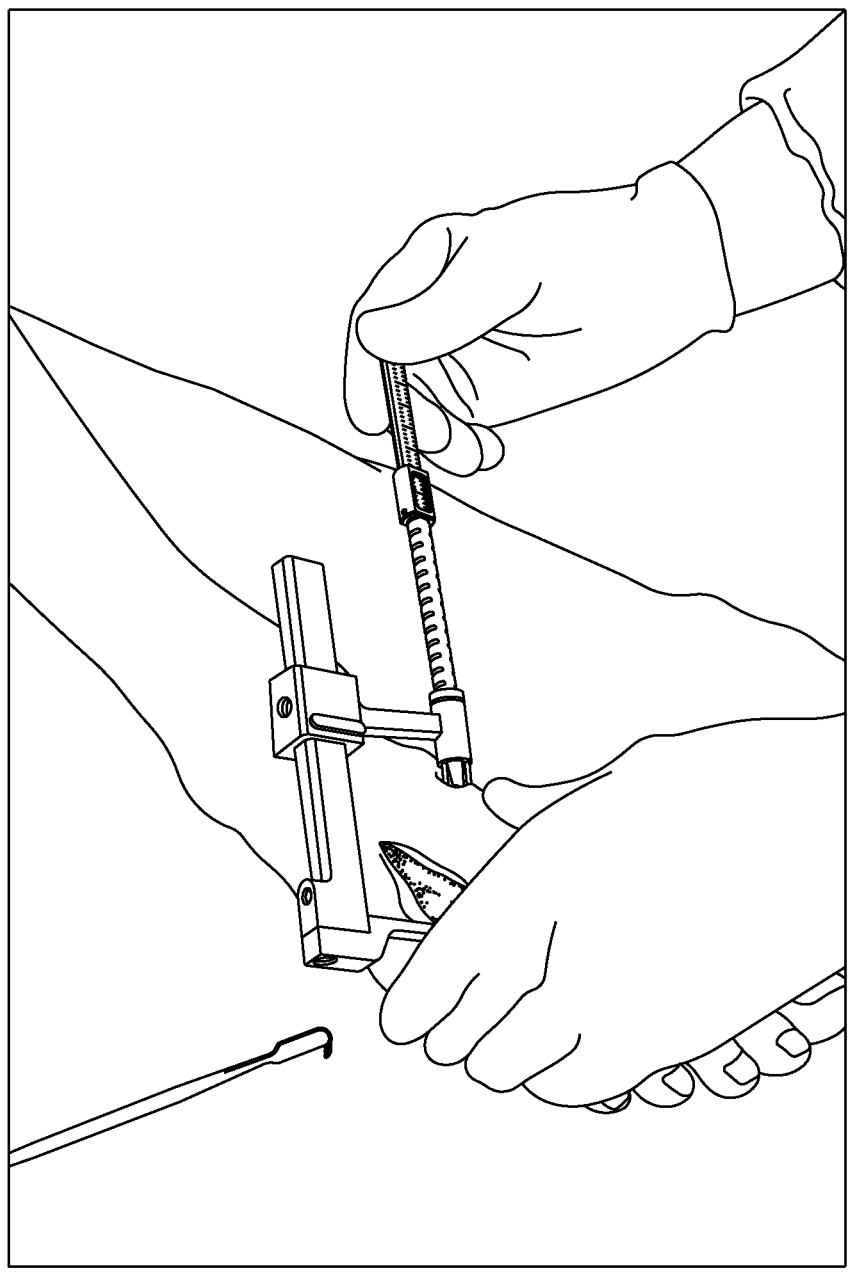

[Screw length determination]—Next, with the K-wire in place, the K-wire guiding sleeve 20 is removed and a depth gage 60 is inserted through the guide housing 116 and over the K-wire to measure the depth of the K-wire inside the bone (see FIG. 27D and block 507 of FIG. 26). The measured depth of the K-wire is the length of the bone screw to be used.

Figure 27E:
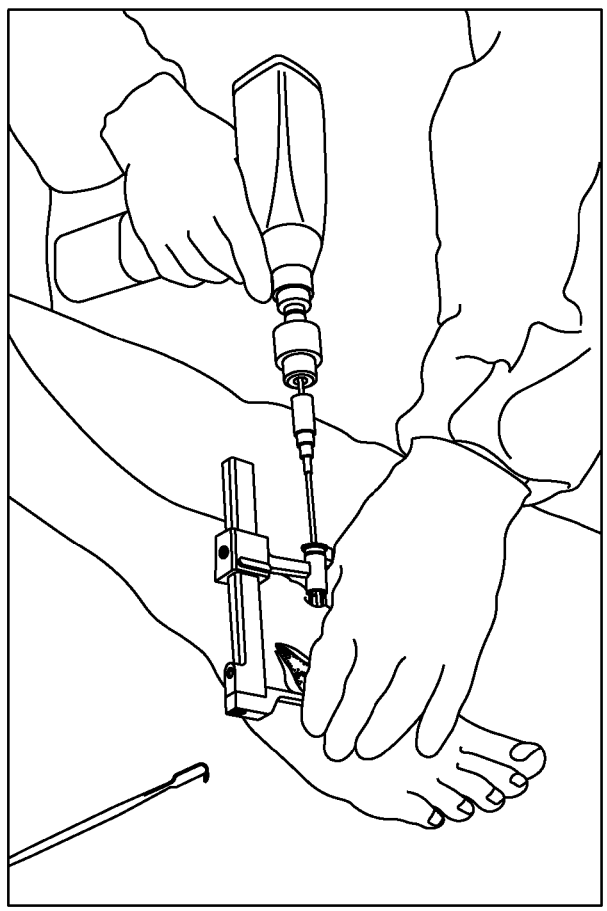
Figure 27F:
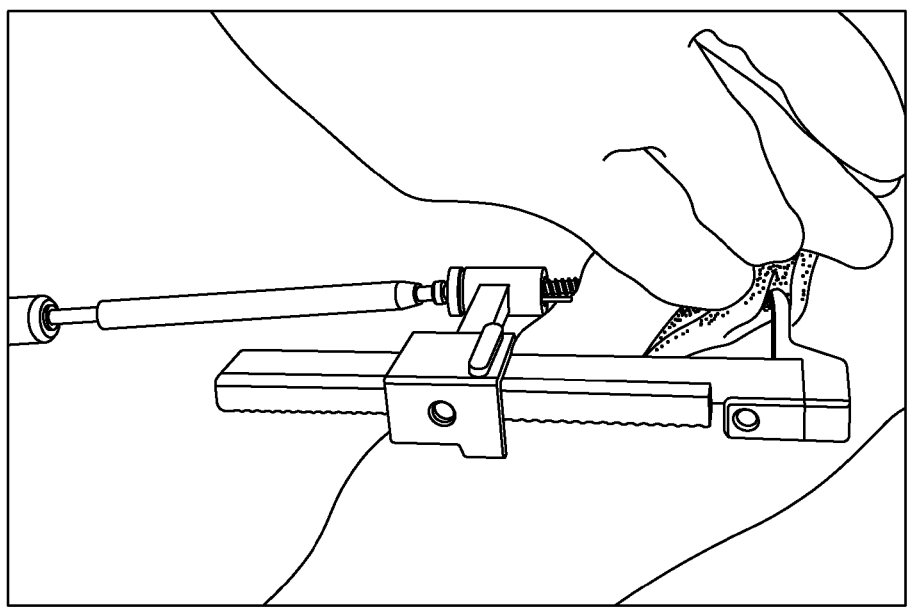

[Hole preparation]—A drill-guiding sleeve 20 is then placed in the guide housing 116 and a cannulated drill is used to pre-drill over the K-wire for screw placement (see FIG. 27E and block 508 of FIG. 26). As discussed before, the K-wire sleeve and the drill sleeve are essentially the same except that the drill sleeve has a larger diameter bore 23. The drill should be of the appropriate diameter for the bone screw that will be used and the diameter of the bore 23 in the drill sleeve should be appropriate size for the drill to ensure proper centering of the drill. If a 3.7 mm screw is to be used, a 2.6 mm cannulated drill is used for the pre-drill. If a 4.5 mm screw is to be used, then a 3.2 mm cannulated drill is used. If arthrodesis or lagging of the screw is desired, the appropriate over-drill (3.7 mm or 4.5 mm) is required to the desired depth. If head countersinking is required, the head drill must be used after the depth gage measurement is made. With the drill bit in the bone, an external imaging can be used to verify that proper depth was drilled (see block 509 of FIG. 26).

[Screw placement]—Once the bone is drilled, the drill bit, the K-wire and the drill-guiding sleeve are removed. At this point, the drill guide assembly 100 is still keeping the bones in reduction and a bone screw of appropriate diameter is screwed or threaded into the bones through the hole 117 in the guide housing 116 until the bone screw is fully seated on the medial cuneiform (see FIG. 27F and block 510 of FIG. 26). If the bone determined to be soft and additional stability is required for the head of the screw, a washer may be placed on the screw prior to insertion. The screw is inserted utilizing the 2.5 mm hex driver for the 3.7 mm screws and the 3.5 mm hex driver for the 4.5 mm screws. Once the bone screw is in place, the drill guide assembly 100 is removed by releasing the ratcheting mechanism (see block 511 of FIG. 26).

Although the drill guide assembly 100 of the present disclosure is configured and adapted to be well suited for the Lisfranc injury repair procedure described above, the drill guide assembly 100 can be used to reduce and install bone screws through fractured bone pieces generally. For example, the drill guide assembly 100 can be used in the repair of bone fractures in the ankle, wrist, etc. The dimensions of the various components of the drill guide assembly 100 can be appropriately varied to accommodate different sizes of the bones involved.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention. The scope of the invention disclosed herein is to be limited only by the following claims.

What is claimed is:

1. A method for repairing a Lisfranc injury between a second metatarsal and medial cuneiform comprising the steps of:
   (a) providing a drill guide assembly device comprising:
      an elongated body having first and second ends;
      a first arm member extending from said first end of the elongated body;
      a second arm member extending from said elongated body and configured and adapted to be longitudinally movable along said elongated body;
      one of the two arm members provided with a guide housing and the other of the two arm members having a generally curved tip portion; and
      a sleeve having a longitudinal bore, wherein said guide housing is configured and adapted to removably receive said sleeve, wherein said guide housing is provided with at least one spike extending towards the other of the two arm members whereby one or more bone pieces positioned between the first and second arm members is secured between said at least one spike and said other of the two arm member's outer end by moving the second arm member towards the first arm member;

(b) making an incision to access said Lisfranc injury site;

(c) placing said curved tip portion of one arm member between the second metatarsal and third metatarsal base;

(d) placing said at least one spike on the medial side of the medial cuneiform in desired alignment with the curved tip portion by closing the two arm members;

(e) reducing the second metatarsal and the medial cuneiform by compressing the two arm members;

(f) inserting a first sleeve into the guide housing, said first sleeve configured and adapted for receiving a guide wire;

(g) drilling a guide wire through the medial cuneiform and the second metatarsal in an alignment guided by the first sleeve to a desired depth which is until the guide wire hits the curved tip portion;

(h) removing the first sleeve and measuring said depth of the guide wire for determining a proper length for a bone screw for securing the second metatarsal and the medial cuneiform;

(i) inserting a second sleeve into the guide housing, said second sleeve configured and adapted for receiving a cannulated drill bit;

(j) drilling a hole through the medial cuneiform and the second metatarsal using the guide wire as a guide;

(k) securing the medial cuneiform to the second metatarsal by threading a bone screw into said drilled hole; and (l) removing the drill guide assembly device.

2. The method of claim 1, wherein after the step (d), further comprising a step of verifying the desired alignment of the two arm members by inserting a blunt trocar in the guide housing and verifying the desired alignment with an external imaging technology before reducing the second metatarsal and the medial cuneiform.

3. The method of claim 1, wherein after drilling the guide wire into the bones, further comprising a step of verifying said alignment of the guide wire by an external imaging technology.

4. The method of claim 1, further comprising verifying said drill depth by external imaging after drilling a cannulated drill bit into the fracture bones.

5. The method of claim 1, wherein the generally curved tip portion curves toward the guide housing provided on one of the two arm members.

6. A method for positioning a passageway in two neighboring bones comprising the steps of:

(a) providing a device for guiding and positioning a guide wire or a drill to a point on a first neighboring bone's surface where the passageway is to begin, said device comprising:

an elongated body having first and second ends;

a first arm member extending from said first end of the elongated body and terminating at an outer end;

a second arm member extending from said elongated body and having a base portion and an outer end tip, wherein the base portion is configured and adapted to engage the elongated body and allow the second arm member to be longitudinally movable along said elongated body, said second arm member extending from the elongated body in the same direction as the first arm member and terminating at the outer end tip;

a guide housing provided on the first arm member at the first arm member's outer end that is away from the elongated body, the guide housing comprising: a cylindrical shape with a sleeve-receiving bore extending longitudinally therethrough and defining an inner surface; and an annular groove provided on the outer surface of the guide housing; and a substantially cylindrical-shaped sleeve extending between a first end and a second end and removably received in said guide housing's bore, the sleeve comprising:

a flared head portion provided at the first end for stopping the sleeve when the sleeve is inserted into the guide housing;

a retention tab extending longitudinally toward the second end from the flared head portion for cooperating with the guide housing for retaining the sleeve in the guide housing, wherein the retention tab is provided with a spring-loaded detent that cooperates with the annular groove on the outer surface of the guide housing for retaining the sleeve in the guide housing; and a longitudinal bore, wherein said guide housing is provided with at least one spike extending towards the first arm member whereby one or more bone pieces positioned between the first and second arm members is secured between said at least one spike and said first arm's outer end by moving the second arm member towards the first arm member;

(b) making an incision to access said two neighboring bones;

(c) placing said first and second arm members around the two neighboring bones by placing said at least one spike on one of the two neighboring bones;

(d) inserting a first sleeve into the guide housing, said first sleeve configured and adapted for receiving a guide wire;

(e) reducing the two neighboring bones by compressing the first and second arm members;

(f) drilling a guide wire through the two neighboring bones in an alignment guided by the first sleeve to a desired depth which is until the guide wire hits the outer end tip;

(g) measuring said depth of the guide wire for determining proper length for a bone screw for securing the two neighboring bones;

(h) drilling a cannulated drill bit into the two neighboring bones to a drill depth using the guide wire as a guide; and (i) threading a bone screw into the two neighboring bones, said bone screw having a length matching the measured depth of the guide wire.

7. The method of claim 6, wherein after the step (c), further comprising a step of verifying the desired alignment of the two arm members by inserting a blunt trocar in the guide housing and verifying the desired alignment with an external imaging technology before reducing the two neighboring bones.

8. The method of claim 6, wherein after drilling the guide wire into the bones, further comprising a step of verifying said alignment of the guide wire by using an external imaging technology.

9. The method of claim 6, further comprising verifying said drill depth by external imaging technology.

10. The method of claim 6, wherein the outer end tip of the second arm member is curved toward the guide housing provided on the first arm member.

* * * * *